(12) United States Patent
Dunn et al.

(10) Patent No.: US 6,653,091 B1
(45) Date of Patent: *Nov. 25, 2003

(54) METHOD AND DEVICE FOR PREDICTING PHYSIOLOGICAL VALUES

(75) Inventors: Timothy C. Dunn, San Francisco, CA (US); Yalia Jayalakshmi, Sunnyvale, CA (US); Ronald T. Kurnik, Foster City, CA (US); Matthew J. Lesho, San Mateo, CA (US); Jonathan James Oliver, Oakland, CA (US); Russell O. Potts, San Francisco, CA (US); Janet A. Tamada, Mountain View, CA (US); Steven Richard Waterhouse, San Francisco, CA (US); Charles W. Wei, Fremont, CA (US)

(73) Assignee: Cyngnus, Inc., Redwood City, CA (US)

( * ) Notice: Subject to any disclaimer, the term of this patent is extended or adjusted under 35 U.S.C. 154(b) by 201 days.

This patent is subject to a terminal disclaimer.

(21) Appl. No.: 09/911,341

(22) Filed: Jul. 23, 2001

Related U.S. Application Data

(63) Continuation of application No. 09/405,976, filed on Sep. 27, 1999, now Pat. No. 6,326,160, which is a continuation-in-part of application No. 09/241,929, filed on Feb. 1, 1999, now abandoned, which is a continuation-in-part of application No. 09/198,039, filed on Nov. 23, 1998, now abandoned, which is a continuation-in-part of application No. 09/163,856, filed on Sep. 30, 1998, now Pat. No. 6,180,416.

(51) Int. Cl.$^7$ .............................................. G01N 33/66
(52) U.S. Cl. ..................... 435/14; 204/400; 204/403; 422/82.01; 422/82.02; 435/25; 435/176; 435/287.1; 435/817; 436/149; 436/150; 436/151; 436/518; 436/525; 436/806
(58) Field of Search ................. 422/82.01, 82.02; 204/400, 403; 435/14, 25, 176, 287.1, 817; 436/149, 150, 151, 518, 525, 806

(56) References Cited

U.S. PATENT DOCUMENTS

| 5,279,543 A | 1/1994 | Glikfeld et al. |
|---|---|---|
| 5,362,307 A | 11/1994 | Guy et al. |
| 5,636,632 A | 6/1997 | Bommamman et al. |
| 5,730,714 A | 3/1998 | Guy et al. |
| 5,735,273 A | 4/1998 | Kurnik et al. |
| 5,771,890 A | 6/1998 | Tamada |
| 5,827,183 A | 10/1998 | Kurnik et al. |
| 5,954,685 A | 9/1999 | Tierney |
| 5,989,409 A | 11/1999 | Kurnik et al. |
| 6,180,416 B1 | 1/2001 | Kurnik et al. |

FOREIGN PATENT DOCUMENTS

| WO | WO 95/02357 | 1/1995 |
|---|---|---|
| WO | WO 96/00109 | 1/1996 |
| WO | WO 96/00110 | 1/1996 |
| WO | WO 96/35370 | 11/1996 |
| WO | WO 97/02811 | 1/1997 |
| WO | WO 97/10356 | 3/1997 |
| WO | WO 97/10499 | 3/1997 |
| WO | WO 97/24059 | 7/1997 |
| WO | WO 98/42252 | 10/1998 |
| WO | WO 99/58050 | 11/1999 |
| WO | WO 99/58051 | 11/1999 |
| WO | WO 99/58190 | 11/1999 |
| WO | WO 99/58973 | 11/1999 |

OTHER PUBLICATIONS

Alcock et al., "Continuous Analyte Monitoring to Aid Clinical Practice," *I.E.E.E. Engineering in Medicine & Biology* 13:(3):319–325 (1994).

(List continued on next page.)

*Primary Examiner*—Christopher L. Chin
(74) *Attorney, Agent, or Firm*—Barbara G. McClung; Gary R. Fabian

(57) ABSTRACT

The invention relates generally to methods, systems, and devices for measuring the concentration of target analytes present in a biological system using a series of measurements obtained from a monitoring system and a Mixtures of Experts (MOE) algorithm. In one embodiment, the present invention describes a method for measuring blood glucose in a subject.

23 Claims, 9 Drawing Sheets

OTHER PUBLICATIONS

Barlow, T.W., "Feed–Forward Neural Networks for Secondary Structure Prediction," *Journal of Molecular Graphics* 13:175–183 (1995).

Ghahramani, Z. And Wolpert, D.M., "Modular Decomposition in Visuomotor Learning," *Nature* 386(6623):392–395 (1997).

Hamilton, J.D. and Susmel, Raul, "Autoregressive Conditional Heteroskedasticity and Changes in Regime," *Journal of Econometrics* 64:307–333 (1994).

Hu et al., "Customized ECG Beat Classifier Using Mixture of Experts," *Proceedings of the 1995 IEEE Workshop* pp. 459–464 (1995).

Jordan et al., "Hierarchical Mixtures of Experts and the EM Algorithm," *Neural Comput.* 6(2):181–214 (1994).

Waterhouse, Steven Richard, "Classification and Regression Using Mixtures of Experts," *Jesus College, Cambridge and Department of Engineering, University of Cambridge*, Oct. 1997.

Waterhouse et al., in: D.S. Touretzky (Ed.) "Bayesian Methods for Mixtures of Experts," *Advances in Neural Information Processing Systems MIT Press.* Cambridge MA. 8:351–357 (1996).

Weigend et al., "Nonlinear Gated Experts for Time Series: Discovering Regimes and Avoiding Overfitting," *International Journal of Neural Systems* 6(4):373–399 (1995).

METHOD AND DEVICE FOR PREDICTING PHYSIOLOGICAL VALUES

CROSS-REFERENCE TO RELATED APPLICATIONS

This application is a continuation of U.S. patent application Ser. No. 09/405,976, filed Sep. 27, 1999, now U.S. Pat. No. 6,326,160, which is a continuation-in-part of U.S. patent application Ser. No. 09/241,929, filed Feb. 1, 1999, now abandoned, which is a continuation-in-part of U.S. patent application Ser. No. 09/198,039, filed Nov. 23, 1998, now abandoned, which is a continuation-in-part of U.S. patent application Ser. No. 09/163,856, filed Sep. 30, 1998, now U.S. Pat. No. 6,180,416; priority is claimed to these applications under 35 U.S.C. §120, and these applications are herein incorporated by reference in their entireties.

FIELD OF THE INVENTION

The invention relates generally to a method and device for measuring the concentration of target chemical analytes present in a biological system. More particularly, the invention relates to a method and monitoring systems for predicting a concentration of an analyte using a series of measurements obtained from a monitoring system and a Mixtures of Experts (MOE) algorithm.

BACKGROUND OF THE INVENTION

The Mixtures of Experts model is a statistical method for classification and regression (Waterhouse, S., "*Classification and Regression Using Mixtures of Experts,* October 1997, Ph.D. Thesis, Cambridge University). Waterhouse discusses Mixtures of Experts models from a theoretical perspective and compares them with other models, such as, trees, switching regression models, modular networks. The first extension described in Waterhouse's thesis is a constructive algorithm for learning model architecture and parameters, which is inspired by recursive partitioning. The second extension described in Waterhouse's thesis uses Bayesian methods for learning the parameters of the model. These extensions are compared empirically with the standard Mixtures of Experts model and with other statistical models on small to medium sized data sets. Waterhouse also describes the application of the Mixtures of Experts framework to acoustic modeling within a large vocabulary speech recognition system.

The Mixtures of Experts model has been employed in protein secondary structure prediction (Barlow, T. W., *Journal Of Molecular Graphics,* 13(3), p. 175–183, 1995). In this method input data were clustered and used to train a series different networks. Application of a Hierarchical Mixtures of Experts to the prediction of protein secondary structure was shown to provide no advantages over a single network.

Mixtures of Experts algorithms have also been applied to the analysis of a variety of different kinds of data sets including the following: human motor systems (Ghahramani, Z. and Wolpert, D. M., *Nature,* 386(6623) :392–395, 1997); and economic analysis (Hamilton, J. D. and Susmel, R., *Journal of Economnetrics,* 64(1–2) :307–333, 1994).

SUMMARY OF THE INVENTION

The present invention provides a method and device (for example, a monitoring or sampling system) for continually or continuously measuring the concentration of an analyte present in a biological system. The method entails continually or continuously detecting a raw signal from the biological system, wherein the raw signal is specifically related to the analyte. A calibration step is performed to correlate the raw signal with a measurement value indicative of the concentration of analyte present in the biological system. These steps of detection and calibration are used to obtain a series of measurement values at selected time intervals. Once the series of measurement values is obtained, the method of the invention provides for the prediction of a measurement value using a Mixtures of Experts (MOE) algorithm.

The raw signal can be obtained using any suitable sensing methodology including, for example, methods which rely on direct contact of a sensing apparatus with the biological system; methods which extract samples from the biological system by invasive, minimally invasive, and non-invasive sampling techniques, wherein the sensing apparatus is contacted with the extracted sample; methods which rely on indirect contact of a sensing apparatus with the biological system; and the like. In preferred embodiments of the invention, methods are used to extract samples from the biological sample using minimally invasive or non-invasive sampling techniques. The sensing apparatus used with any of the above-noted methods can employ any suitable sensing element to provide the raw signal including, but not limited to, physical, chemical, electrochemical, photochemical, spectrophotometric, polarimetric, calorimetric, radiometric, or like elements. In preferred embodiments of the invention, a biosensor is used which comprises an electrochemical sensing element.

In one particular embodiment of the invention, the raw signal is obtained using a transdermal sampling system that is placed in operative contact with a skin or mucosal surface of the biological system. The sampling system transdermally extracts the analyte from the biological system using any appropriate sampling technique, for example, iontophoresis. The transdermal sampling system is maintained in operative contact with the skin or mucosal surface of the biological system to provide for continual or continuous analyte measurement.

In a preferred embodiment of the invention, a Mixtures of Experts algorithm is used to predict measurement values. The general Mixtures of Experts algorithm is represented by the following series of equations: where the individual experts have a linear form:

$$An = \sum_{i=1}^{n} An_i w_i \quad (1)$$

wherein (An) is an analyte of interest, n is the number of experts, $An_i$ is the analyte predicted by Expert i; and $w_i$ is a parameter, and the individual experts $An_i$ are further defined by the expression shown as Equation (2)

$$An_i = \sum_{j=1}^{m} a_{ij} p_j + z_i \quad (2)$$

wherein, $An_i$ is the analyte predicted by Expert i; $P_j$ is one of m parameters, m is typically less than 100; $a_{ij}$ are coefficients; and $z_i$ is a constant; and further where the weighting value, $w_i$, is defined by the formula shown as Equation (3).

$$w_i = \frac{e^{d_i}}{\left[\sum_{k=1}^{n} e^{d_k}\right]} \quad (3)$$

where e refers to the exponential function and the $d_k$ (note that the $d_i$ in the numerator of Equation 3 is one of the $d_k$) are a parameter set analogous to Equation 2 that is used to determine the weights $w_i$. The $d_k$ are given by Equation 4.

$$d_k = \sum_{j=1}^{m} \alpha_{jk} P_j + \omega_k \quad (4)$$

where $\alpha_{jk}$ is a coefficient, $P_j$ is one of m parameters, and where $\omega_k$ is a constant.

Another object of the invention to use the Mixtures of Experts algorithm of the invention to predict blood glucose values. In one aspect, the method of the invention is used in conjunction with an iontophoretic sampling device that provides continual or continuous blood glucose measurements. In one embodiment the Mixtures of Experts algorithm is essentially as follows: where the individual experts have a linear form $$BG = w_1 BG_1 + w_2 BG_2 + w_3 BG_3 \quad (5)$$

wherein (BG) is blood glucose, there are three experts (n=3) and $BG_i$ is the analyte predicted by Expert i; $w_i$ is a parameter, and the individual Experts $BG_i$ are further defined by the expression shown as Equations 6, 7, and 8

$$BG_1 = p_1(\text{time}) + q_1(\text{active}) + r_1(\text{signal}) + s_1(BG|cp) + t_1 \quad (6)$$

$$BG_2 = p_2(\text{time}) + q_2(\text{active}) + r_2(\text{signal}) + s_2(BG|cp) + t_2 \quad (7)$$

$$BG_3 = p_3(\text{time}) + q_3(\text{active}) + r_3(\text{signal}) + s_3(BG|cp) + t_3 \quad (8)$$

wherein, $BG_i$ is the analyte predicted by Expert i; parameters include, time (elapsed time since the sampling system was placed in operative contact with said biological system), active (active signal), signal (calibrated signal), and BG/cp (blood glucose value at a calibration point); $p_i$, $q_i$, $r_i$, and $s_i$ are coefficients; and $t_i$ is a constant; and further where the weighting value, $w_i$, is defined by the formulas shown as Equations 9, 10, and 11

$$w_1 = \frac{e^{d_1}}{e^{d_1} + e^{d_2} + e^{d_3}} \quad (9)$$

$$w_2 = \frac{e^{d_2}}{e^{d_1} + e^{d_2} + e^{d_3}} \quad (10)$$

$$w_3 = \frac{e^{d_3}}{e^{d_1} + e^{d_2} + e^{d_3}} \quad (11)$$

where e refers to the exponential function and $d_i$ is a parameter set (analogous to Equations 6, 7, and 8) that are used to determine the weights $w_i$, given by Equations 9, 10, and 11, and $$d_1 = \tau_1(\text{time}) + \beta_1(\text{active}) + \gamma_1(\text{signal}) + \delta_1(BG|cp) + \epsilon_1 \quad (12)$$

$$d_2 = \tau_2(\text{time}) + \beta_2(\text{active}) + \gamma_2(\text{signal}) + \delta_2(BG|cp) + \epsilon_2 \quad (13)$$

$$d_3 = \tau_3(\text{time}) + \beta_3(\text{active}) + \gamma_3(\text{signal}) + \delta_3(BG|cp) + \epsilon_3 \quad (14)$$

where $\tau_i$, $\beta_i$, $\gamma_i$ and $\delta_i$ are coefficients, and where $\epsilon_i$ is a constant.

In another embodiment for the prediction of blood glucose values, the Mixtures of Experts algorithm is essentially as follows: where the individual experts have a linear form $$BG = w_1 BG_1 + w_2 BG_2 + w_3 BG_3 \quad (15)$$

wherein (BG) is blood glucose, there are three experts (n=3) and $BG_i$ is the analyte predicted by Expert i; $w_i$ is a parameter, and the individual Experts $BG_i$ are further defined by the expression shown as Equations 16, 17, and 18

$$BG_1 = p_1(\text{time}_c) + q_1(\text{active}) + r_1(\text{signal}) + s_1(BG|cp) + t_1 \quad (16)$$

$$BG_2 = p_2(\text{time}_c) + q_2(\text{active}) + r_2(\text{signal}) + s_2(BG|cp) + t_2 \quad (17)$$

$$BG_3 = p_3(\text{time}_c) + q_3(\text{active}) + r_3(\text{signal}) + s_3(BG|cp) + t_3 \quad (18)$$

wherein, $BG_i$ is the analyte predicted by Expert i; parameters include, $\text{time}_c$ (elapsed time since calibration of said sampling system), active (active signal), signal (calibrated signal), and BG/cp (blood glucose value at a calibration point); $p_i$, $q_i$, $r_i$, and $s_i$ are coefficients; and $t_i$ is a constant; and further where the weighting value, $w_i$, is defined by the formulas shown as Equations 19, 20, and 21

$$w_1 = \frac{e^{d_1}}{e^{d_1} + e^{d_2} + e^{d_3}} \quad (19)$$

$$w_2 = \frac{e^{d_2}}{e^{d_1} + e^{d_2} + e^{d_3}} \quad (20)$$

$$w_3 = \frac{e^{d_3}}{e^{d_1} + e^{d_2} + e^{d_3}} \quad (21)$$

where e refers to the exponential function and $d_i$ is a parameter set (analogous to Equations 6, 7, and 8) that are used to determine the weights $w_i$, given by Equations 19, 20, and 21, and $$d_1 = \tau_1(\text{time}_c) + \beta_1(\text{active}) + \gamma_1(\text{signal}) + \delta_1(BG|cp) + \epsilon_1 \quad (22)$$

$$d_2 = \tau_2(\text{time}_c) + \beta_2(\text{active}) + \gamma_2(\text{signal}) + \delta_2(BG|cp) + \epsilon_2 \quad (23)$$

$$d_3 = \tau_3(\text{time}_c) + \beta_3(\text{active}) + \gamma_3(\text{signal}) + \delta_3(BG|cp) + \epsilon_3 \quad (24)$$

where $\tau_i$, $\beta_i$, $\gamma_i$ and $\delta_i$ are coefficients, and where $\epsilon_i$ is a constant.

Parameters can be substituted, and/or other parameters can be included in these calculations, for example, time parameters can be varied (e.g., as described above, elapsed time since the sampling system was placed in contact with a biological system, or elapsed time since the sampling system was calibrated) or multiple time parameters can be used in the same equation where these parameters are appropriately weighted. Further parameters include, but are not limited to, temperature, iontophoretic voltage, and skin conductivity. In addition, a calibration check can be used to insure an efficacious calibration.

A further object of the invention to provide a method for measuring an analyte, for example, blood glucose, in a subject. In one embodiment, the method entails operatively contacting a glucose sensing apparatus with the subject to detect blood glucose and thus obtain a raw signal from the sensing apparatus. The raw signal is specifically related to the glucose, and is converted into a measurement value indicative of the subject's blood glucose concentration using a calibration step. In one aspect of the invention, the sensing apparatus is a near-IR spectrometer. In another aspect of the invention, the sensing means comprises a biosensor having an electrochemical sensing element.

It is also an object of the invention to provide a monitoring system for continually or continuously measuring an analyte present in a biological system. The monitoring system is formed from the operative combination of a sampling means, a sensing means, and a microprocessor means which controls the sampling means and the sensing means. The sampling means is used to continually or continuously extract the analyte from the biological system across a skin or mucosal surface of said biological system. The sensing means is arranged in operative contact with the analyte extracted by the sampling means, such that the sensing means can obtain a raw signal from the extracted analyte which signal is specifically related to the analyte. The microprocessor means communicates with the sampling means and the sensing means, and is used to: (a) control the sampling means and the sensing means to obtain a series of raw signals at selected time intervals during a continual or continuous measurement period; (b) correlate the raw signals with measurement values indicative of the concentration of analyte present in the biological system; and (c) predict a measurement value using the Mixtures of Experts algorithm. In one aspect, the monitoring system uses an iontophoretic current to extract the analyte from the biological system.

It is a further object of the invention to provide a monitoring system for measuring blood glucose in a subject. The monitoring system is formed from an operative combination of a sensing means and a microprocessor means. The sensing means is adapted for operative contact with the subject or with a glucose-containing sample extracted from the subject, and is used to obtain a raw signal specifically related to blood glucose in the subject. The microprocessor means communicates with the sensing means, and is used to: (a) control the sensing means to obtain a series of raw signals (specifically related to blood glucose) at selected time intervals; (b) correlate the raw signals with measurement values indicative of the concentration of blood glucose present in the subject; and (c) predict a measurement value using the Mixtures of Experts algorithm.

In a further aspect, the monitoring system comprises a biosensor having an electrochemical sensing element. In another aspect, the monitoring system comprises a near-IR spectrometer.

Additional objects, advantages and novel features of the invention will be set forth in part in the description which follows, and in part will become apparent to those skilled in the art upon examination of the following, or may be learned by practice of the invention.

DETAILED DESCRIPTION OF THE PREFERRED EMBODIMENTS

Figure 1A:
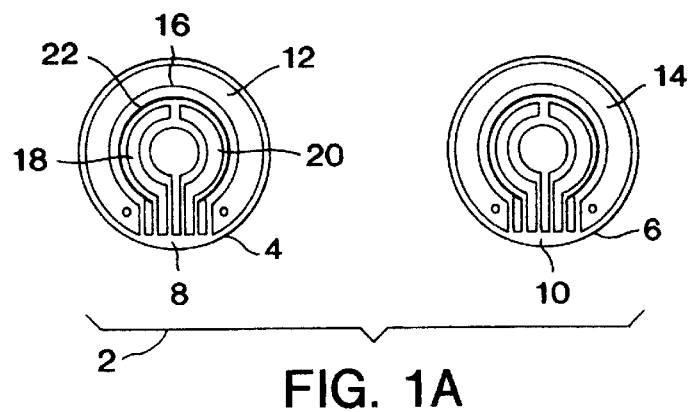
FIG. 1A depicts a top plan view of an iontophoretic collection reservoir and electrode assembly for use in a transdermal sampling device constructed according to the present invention.

Before describing the present invention in detail, it is to be understood that this invention is not limited to particular compositions or biological systems, as such may vary. It is also to be understood that the terminology used herein is for the purpose of describing particular embodiments only, and is not intended to be limiting.

It must be noted that, as used in this specification and the appended claims, the singular forms "all", "an" and "the" include plural referents unless the content clearly dictates otherwise. Thus, for example, reference to "an analyte" includes mixtures of analytes, and the like.

All publications, patents and patent applications cited herein, whether supra or infra, are hereby incorporated by reference in their entirety.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

1.0.0 Definitions

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device" or "sampling system" refers to any device for obtaining a sample from a biological system for the purpose of determining the concentration of an analyte of interest. As used herein, the term "sampling" means invasive, minimally invasive or non-invasive extraction of a substance from the biological system, generally across a membrane such as skin or mucosa. The membrane can be natural or artificial, and can be of plant or animal nature, such as natural or artificial skin, blood vessel tissue, intestinal tissue, and the like. Typically, the sampling means are in operative contact with a "reservoir," or "collection reservoir," wherein the sampling means is used for extracting the analyte from the biological system into the reservoir to obtain the analyte in the reservoir. A "biological system" includes both living and artificially maintained systems. Examples of minimally invasive and noninvasive sampling techniques include iontophoresis, sonophoresis, suction, electroporation, thermal poration, passive diffusion, microfine (miniature) lances or cannulas, subcutaneous implants or insertions, and laser devices. Sonophoresis uses ultrasound to increase the permeability of the skin (see, e.g., Menon et al. (1994) *Skin Pharmacology* 7:130–139). Suitable sonophoresis sampling systems are described in International Publication No. WO 91/12772, published Sep. 5, 1991. Passive diffusion sampling devices are described, for example, in International Publication Nos.: WO 97/38126 (published Oct. 16, 1997); WO 97/42888, WO 97/42886, WO 97/42885, and WO 97/42882 (all published Nov. 20, 1997); and WO 97/43962 (published Nov. 27, 1997). Laser devices use a small laser beam to burn a hole through the upper layer of the patient's skin (see, e.g., Jacques et al. (1978) *J. Invest. Dermatology* 88:88–93). Examples of invasive sampling techniques include traditional needle and syringe or vacuum sample tube devices.

The term "collection reservoir" is used to describe any suitable containment means for containing a sample extracted from a biological system. For example, the collection reservoir can be a receptacle containing a material which is ionically conductive (e.g., water with ions therein), or alternatively, it can be a material, such as, a sponge-like material or hydrophilic polymer, used to keep the water in place. Such collection reservoirs can be in the form of a hydrogel (for example, in the form of a disk or pad). Hydrogels are typically referred to as "collection inserts." Other suitable collection reservoirs include, but are not limited to, tubes, vials, capillary collection devices, cannulas, and miniaturized etched, ablated or molded flow paths.

A "housing" for the sampling system can further include suitable electronics (e.g., microprocessor, memory, display and other circuit components) and power sources for operating the sampling system in an automatic fashion.

A "monitoring system," as used herein, refers to a system useful for continually or continuously measuring a physiological analyte present in a biological system. Such a system typically includes, but is not limited to, sampling means, sensing means, and a microprocessor means in operative communication with the sampling means and the sensing means.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "continual measurement" intends a series of two or more measurements obtained from a particular biological system, which measurements are obtained using a single device maintained in operative contact with the biological system over the time period in which the series of measurements is obtained. The term thus includes continuous measurements.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term "transdermal extraction," or "transdermally extracted" intends any noninvasive, or at least minimally invasive sampling method, which entails extracting and/or transporting an analyte from beneath a tissue surface across skin or mucosal tissue. The term thus includes extraction of an analyte using iontophoresis (reverse iontophoresis), electroosmosis, sonophoresis, microdialysis, suction, and passive diffusion. These methods can, of course, be coupled with application of skin penetration enhancers or skin permeability enhancing technique such as tape stripping or pricking with micro-needles. The term "transdermally extracted" also encompasses extraction techniques which employ thermal poration, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example, by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode).

The term "reverse iontophoresis" refers to the movement of a substance from a biological fluid across a membrane by way of an applied electric potential or current. In reverse iontophoresis, a reservoir is provided at the tissue surface to receive the extracted material.

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing means," or "biosensor device" encompasses any device that can be used to measure the concentration of an analyte, or derivative thereof, of interest. Preferred sensing devices for detecting blood analytes generally include electrochemical devices and chemical devices. Examples of electrochemical devices include the Clark electrode system (see, e.g., Updike, et al., (1967) Nature 214:986–988), and other amperometric, coulometric, or potentiometric electrochemical devices. Examples of chemical devices include conventional enzyme-based reactions as used in the Lifescan® glucose monitor (Johnson and Johnson, New Brunswick, N.J.) (see, e.g., U.S. Pat. No. 4,935,346 to Phillips, et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (Analytical Chemistry 67 (24), 4594–4599, 1995).

The "sensor element" can include components in addition to a biosensor electrode, for example, it can include a "reference electrode," and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit which acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

In one embodiment, the "counter electrode" of the "sensor element" comprises a "bimodal electrode." The term "bimodal electrode" as used herein typically refers to an electrode which is capable of functioning non-simultaneously as, for example, both the counter electrode (of the "sensor element") and the iontophoretic electrode (of the "sampling means").

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof; (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semisolid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

A "laminate", as used herein, refers to structures comprised of at least two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, pressure sensitive adhesives, thermoset adhesives, cyanocrylate adhesives, epoxies, contact adhesives, and heat sensitive adhesives.

A "collection assembly", as used herein, refers to structures comprised of several layers, where the assembly includes at least one collection insert, for example a hydrogel. An example of a collection assembly of the present invention is a mask layer, collection inserts, and a retaining layer where the layers are held in appropriate, functional relationship to each other but are not necessarily a laminate, i.e., the layers may not be bonded together. The layers may, for example, be held together by interlocking geometry or friction.

An "autosensor assembly", as used herein, refers to structures generally comprising a mask layer, collection inserts, a retaining layer, an electrode assembly, and a support tray. The autosensor assembly may also include liners. The layers of the assembly are held in appropriate, functional relationship to each other.

The mask and retaining layers are preferably composed of materials that are substantially impermeable to the analyte (chemical signal) to be detected (e.g., glucose); however, the material can be permeable to other substances. By "substantially impermeable" is meant that the material reduces or eliminates chemical signal transport (e.g., by diffusion). The material can allow for a low level of chemical signal transport, with the proviso that chemical signal that passes through the material does not cause significant edge effects at the sensing electrode.

"Substantially planar" as used herein, includes a planar surface that contacts a slightly curved surface, for example, a forearm or upper arm of a subject. A "substantially planar" surface is, for example, a surface having a shape to which skin can conform, i.e., contacting contact between the skin and the surface.

A "Mixtures of Experts (MOE)" algorithm is used in the practice of the present invention. An example of a Mixtures of Experts algorithm useful in connection with the present invention is represented by the following equations, where the individual experts have a linear form:

$$An = \sum_{i=1}^{n} An_i w_i \quad (1)$$

wherein (An) is an analyte of interest, n is the number of experts, $An_i$ is the analyte predicted by Expert i; and $w_i$ is a parameter, and the individual experts $An_i$ are further defined by the expression shown as Equation (2)

$$An_i = \sum_{j=1}^{m} a_{ij} P_j + z_i \quad (2)$$

wherein, $An_i$ is the analyte predicted by Expert i; $P_j$ is one of m parameters, m is typically less than 100; $a_{ij}$ are coefficients; and $z_i$ is a constant; and further where the weighting value, $w_i$, is defined by the formula shown as Equation (3).

$$w_i = \frac{e^{d_i}}{\left[\sum_{k=1}^{n} e^{d_k}\right]} \quad (3)$$

where e refers to the exponential function the $d_k$ (note that the $d_i$ in the numerator of Equation 3 is one of the $d_k$) are a parameter set analogous to Equation 2 that is used to determine the weights $w_i$. The $d_k$ are given by Equation 4.

$$d_k = \sum_{j=1}^{m} \alpha_{jk} P_j + \omega_k \quad (4)$$

where $\alpha_{jk}$ is a coefficient, $P_j$ is one of m parameters, and where $\omega_k$ is a constant.

The Mixtures of Experts algorithm is a generalized predictive technology for data analysis. This method uses a superposition of multiple linear regressions, along with a switching algorithm, to predict outcomes. Any number of input/output variables are possible. The unknown coefficients in this method are determined by a maximum posterior probability technique.

The method is typically implemented as follows. An experimental data set of input/output pairs is assembled that spans the expected ranges of all variables. These variables are then used to train the Mixtures of Experts (that is, used to determine the unknown coefficients). These coefficients are determined using, for example, the Expectation Maximization method (Dempster, A. P., N. M. Laird, and D. B. Rubin, *J. Royal Statistical Society* (Series B-Methodological) 39:(1), 1977). Once these coefficients are known, the Mixtures of Experts is easily applied to a new data set.

"Parameter" as used herein refers to an arbitrary constant or variable so appearing in a mathematical expression that changing it give various cases of the phenomenon represented (*McGraw-Hill Dictionary of Scientific and Technical Terms*, S. P. Parker, ed., Fifth Edition, McGraw-Hill Inc., 1994). In the context of the GlucoWatch® monitor (Cygnus, Inc., Redwood City, Calif.), a parameter is a variable that influences the value of the blood glucose level as calculated by an algorithm. For the Mixtures of Experts algorithm, these parameters include, but are not limited to, the following: time (e.g., elapsed time since the monitor was applied to a subject; and/or elapsed time since calibration); the active signal; the calibrated signal; the blood glucose value at the calibration point; the skin temperature; the skin conductivity; and the iontophoretic voltage. Changes in the values of any of these parameters can be expected to change the value of the calculated blood glucose value. Parameters can be substituted, and/or other parameters can be included in these calculations, for example, time parameters can be varied (e.g., elapsed time since the sampling system was placed in contact with a biological system, or elapsed time since the sampling system was calibrated) or multiple time parameters can be used in the same equation where these parameters are appropriately weighted.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

"Bias" as used herein refers to the difference between the expected value of an estimator and the true value of a parameter. "Bias" is used in a statistical context, in particular, in estimating the value of a parameter of a probability distribution. For example, in the case of a linear regression wherein y=mx+b, for x=a, the bias at "a" equals (ma+b)−a.

"Decay" as used herein refers to a gradual reduction in the magnitude of a quantity, for example, a current detected using a sensor electrode where the current is correlated to the concentration of a particular analyte and where the detected current gradually reduces but the concentration of the analyte does not.

2.0.0 General Methods

The present invention relates to the analysis of data obtained by use of a sensing device for measuring the concentration of a target analyte present in a biological system. In preferred embodiments, the sensing device comprises a biosensor. In other preferred embodiments, a sampling device is used to extract small amounts of a target analyte from the biological system, and then sense and/or quantify the concentration of the target analyte. Measurement with the biosensor and/or sampling with the sampling device can be carried out in a continual manner. Continual measurement allows for closer monitoring of target analyte concentration fluctuations.

In the general method of the invention, a raw signal is obtained from a sensing device, which signal is related to a target analyte present in the biological system. The raw signal can be obtained using any suitable sensing methodology including, for example, methods which rely on direct contact of a sensing apparatus with the biological system; methods which extract samples from the biological system by invasive, minimally invasive, and non-invasive sampling techniques, wherein the sensing apparatus is contacted with the extracted sample; methods which rely on indirect contact of a sensing apparatus with the biological system; and the like. In preferred embodiments of the invention, methods are used to extract samples from the biological sample using minimally invasive or non-invasive sampling techniques. The sensing apparatus used with any of the above-noted methods can employ any suitable sensing element to provide the signal including, but not limited to, physical, chemical, electrochemical, photochemical, spectrophotometric, polarimetric, colorimetric, radiometric, or like elements. In preferred embodiments of the invention, a biosensor is used which comprises an electrochemical sensing element.

In another embodiment of the invention, a near-IR glucose sensing apparatus is used to detect blood glucose in a subject, and thus generate the raw signal. A number of near-IR glucose sensing devices suitable for use in the present method are known in the art and are readily available. For example, a near-IR radiation diffuse-reflection laser spectroscopy device is described in U.S. Pat. No. 5,267,152 to Yang et al. Similar near-IR spectrometric devices are also described in U.S. Pat. No. 5,086,229 to Rosenthal et al. and U.S. Pat. No. 4,975,581 to Robinson et al. These near-IR devices use traditional methods of reflective or transmissive near infrared (near-IR) analysis to measure absorbance at one or more glucose-specific wavelengths, and can be contacted with the subject at an appropriate location, such as a finger-tip, skin fold, eyelid, or forearm surface to obtain the raw signal.

The raw signal obtained using any of the above-described methodologies is then converted into an analyte-specific value of known units to provide an interpretation of the signal obtained from the sensing device. The interpretation uses a mathematical transformation to model the relationship between a measured response in the sensing device and a corresponding analyte-specific value (in the present invention, a Mixtures of Experts algorithm). Thus, a calibration step is used herein to relate, for example, an electrochemical signal (detected by a biosensor), or near-IR absorbance spectra (detected with a near-IR detector) with the concentration of a target analyte in a biological system.

The predicted analyte values can optionally be used in a subsequent step to control an aspect of the biological system. In one embodiment, predicted analyte values are used to determine when, and at what level, a constituent should be added to the biological system in order to control an aspect of the biological system. In a preferred embodiment, the analyte value can be used in a feedback control loop to control a physiological effect in the biological system.

The above general methods can, of course, be used with a wide variety of biological systems, target analytes, and/or sensing techniques. The determination of particularly suitable combinations is within the skill of the ordinarily skilled artisan when directed by the instant disclosure. Although these methods are broadly applicable to measuring any chemical analyte and/or substance in a biological system, the invention is expressly exemplified for use in a non-invasive, transdermal sampling system which uses an electrochemical biosensor to quantify or qualify glucose or a glucose metabolite.

2.1.0 Obtaining the Raw Signal

The raw signal can be obtained using any sensing device that is operatively contacted with the biological system. Such sensing devices can employ physical, chemical, electrochemical, spectrophotometric, polarimetric, colorimetric, radiometric, or like measurement techniques. In addition, the sensing device can be in direct or indirect contact with the biological system, or used with a sampling device which extracts samples from the biological system using invasive, minimally invasive or non-invasive sampling techniques. In preferred embodiments, a minimally invasive or non-invasive sampling device is used to obtain samples from the biological system, and the sensing device comprises a biosensor with an electrochemical sensing element.

The analyte can be any specific substance or component in a biological system that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate/lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

In order to facilitate detection of the analyte, an enzyme can be disposed in the collection reservoir, or, if several collection reservoirs are used, the enzyme can be disposed in several or all of the reservoirs. The selected enzyme is capable of catalyzing a reaction with the extracted analyte (e.g., glucose) to the extent that a product of this reaction can be sensed, e.g., can be detected electrochemically from the generation of a current which current is detectable and proportional to the concentration or amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, urea with a urease system, cholesterol with a cholesterol oxidase system, and theophylline with a xanthine oxidase system.

In addition, the oxidase enzyme (used for hydrogen peroxidase-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

In particularly preferred embodiments, a sampling device is used to obtain continual transdermal or transmucosal samples from a biological system, and the analyte of interest is glucose. More specifically, a non-invasive glucose monitoring device is used to measure changes in glucose levels in an animal subject over a wide range of glucose concentrations. The sampling method is based on transdermal glucose extraction and the sensing method is based on electrochemical detection technology. The device can be contacted with the biological system continuously, and automatically obtains glucose samples in order to measure glucose concentration at preprogrammed intervals.

Sampling is carried out continually by non-invasively extracting glucose through the skin of the patient using an iontophoretic current. More particularly, an iontophoretic current is applied to a surface of the skin of a subject. When the current is applied, ions or charged molecules pull along other uncharged molecules or particles such as glucose which are drawn into a collection reservoir placed on the surface of the skin. The collection reservoir may comprise any ionically conductive material and is preferably in the form of a hydrogel which is comprised of a hydrophilic material, water and an electrolyte. The collection reservoir may further contain an enzyme which catalyzes a reaction between glucose and oxygen. The enzyme is preferably glucose oxidase (GOx) which catalyzes the reaction between glucose and oxygen and results in the production of hydrogen peroxide. The hydrogen peroxide reacts at a catalytic surface of a biosensor electrode, resulting in the generation of electrons which create a detectable biosensor current (raw signal). Based on the amount of biosensor current created over a given period of time, a measurement is taken, which measurement is related to the amount of glucose drawn into the collection reservoir over a given period of time. In a preferred embodiment the reaction is allowed to continue until substantially all of the glucose in the collection reservoir has been subjected to a reaction and is therefore no longer detectable, and the total biosensor current generated is related to the concentration of glucose in the subject.

When the reaction is complete, the process is repeated and a subsequent measurement is obtained. More specifically, the iontophoretic current is again applied, glucose is drawn through the skin surface into the collection reservoir, and the reaction is catalyzed in order to create a biosensor current. These sampling (extraction) and sensing operations are integrated such that glucose from interstitial fluid directly beneath the skin surface is extracted into the hydrogel collection pad where it contacts the GOx enzyme. The GOx enzyme converts glucose and oxygen in the hydrogel to hydrogen peroxide which diffuses to a Pt-based sensor and reacts with the sensor to regenerate oxygen and form electrons. The electrons generate an electrical signal that can be measured, analyzed, and correlated to blood glucose.

A generalized method for continual monitoring of a physiological analyte is disclosed in International Publication No. WO 97/24059, published Jul. 10, 1997, which publication is incorporated herein by reference. As noted in that publication, the analyte is extracted into a reservoir containing a hydrogel which is preferably comprised of a hydrophilic material of the type described in International Publication No. WO 97/02811, published Jan. 30, 1997, which publication is incorporated herein by reference. Suitable hydrogel materials include polyethylene oxide, polyacrylic acid, polyvinylalcohol and related hydrophilic polymeric materials combined with water to form an aqueous gel.

In the above non-invasive glucose monitoring device, a biosensor electrode is positioned on a surface of the hydrogel opposite the surface contacting the skin. The sensor electrode acts as a detector which detects current generated by hydrogen peroxide in the redox reaction, or more specifically detects current which is generated by the electrons generated by the redox reaction catalyzed by the platinum surface of the electrode. The details of such electrode assemblies and devices for iontophoretic extraction of glucose are disclosed in International Publication No. WO 96/00110, published Jan. 4, 1996, and International Publication No. WO 97/10499, published Mar. 2, 1997, which publications are also incorporated herein by reference.

Figure 1B:
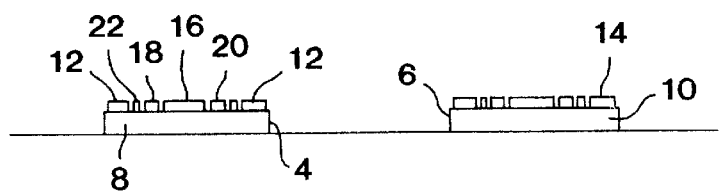
FIG. 1B depicts the side view of the iontophoretic collection reservoir and electrode assembly shown in FIG. 1A.

Referring now to FIGS. 1A and 1B, one example of an iontophoretic collection reservoir and electrode assembly for use in a transdermal sensing device is generally indicated at 2. The assembly comprises two iontophoretic collection reservoirs, 4 and 6, each having a conductive medium 8, and 10 (preferably hydrogel pads), respectively disposed therein. First (12) and second (14) ring-shaped iontophoretic electrodes are respectively contacted with conductive medium 8 and 10. The first iontophoretic electrode 12 surrounds three biosensor electrodes which are also contacted with the conductive medium 8, a working electrode 16, a reference electrode 18, and a counter electrode 20. A guard ring 22 separates the biosensor electrodes from the iontophoretic electrode 12 to minimize noise from the iontophoretic circuit. Conductive contacts provide communication between the electrodes and an associated power source and control means as described in detail below. A similar biosensor electrode arrangement can be contacted with the conductive medium 10, or the medium can not have a sensor means contacted therewith.

Figure 2:
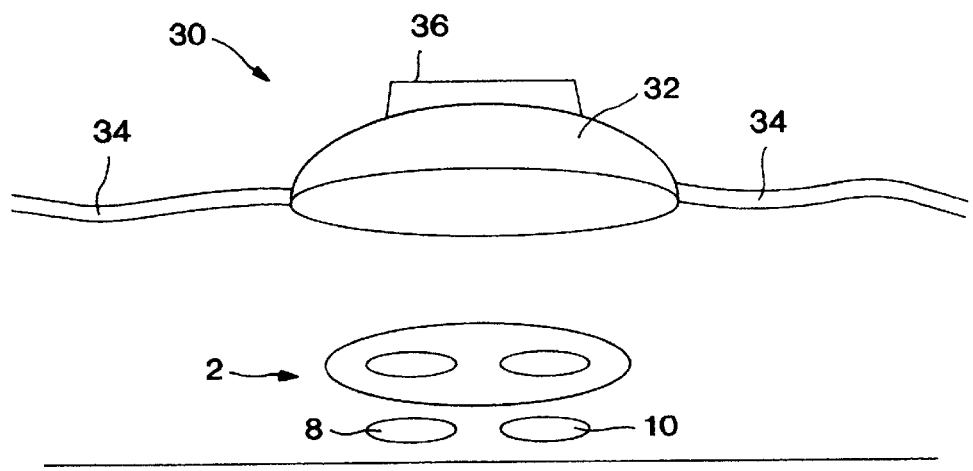
FIG. 2 is a pictorial representation of an iontophoretic sampling device which includes the iontophoretic collection reservoir and electrode assembly of FIGS. 1A and 1B.

Referring now to FIG. 2, the iontophoretic collection reservoir and electrode assembly 2 of FIGS. 1A and 1B is shown in exploded view in combination with a suitable iontophoretic sampling device housing 32. The housing can be a plastic case or other suitable structure which preferably is configured to be worn on a subjects arm in a manner similar to a wrist watch. As can be seen, conductive media 8 and 10 (hydrogel pads) are separable from the assembly 2; however, when the assembly 2 and the housing 32 are assembled to provide an operational iontophoretic sampling device 30, the media are in contact with the electrodes to provide a electrical contact therewith.

A power source (e.g., one or more rechargeable or non-rechargeable batteries) can be disposed within the housing 32 or within the straps 34 which hold the device in contact with a skin or mucosal surface of a subject. In use, an electric potential (either direct current or a more complex waveform) is applied between the two iontophoretic electrodes 12 and 14 such that current flows from the first iontophoretic electrode 12, through the first conductive medium 8 into the skin or mucosal surface, and then back out through the second conductive medium 10 to the second iontophoretic electrode 14. The current flow is sufficient to extract substances including an analyte of interest through the skin into one or both of collection reservoirs 4 and 6. The electric potential may be applied using any suitable technique, for example, the applied current density may be in the range of about 0.01 to 0.5 mA/cm$^2$. In a preferred embodiment, the device is used for continual or continuous monitoring, and the polarity of iontophoretic electrodes 12 and 14 is alternated at a rate of about one switch every 10 seconds to about one switch every hour so that each electrode is alternately a cathode or an anode. The housing 32 can further include an optional temperature sensing element (e.g., a thermistor, thermometer, or thermocouple device) which monitors the temperature at the collection reservoirs to enable temperature correction of sensor signals. The housing can also include an optional conductance sensing element (e.g., an integrated pair of electrodes) which monitors conductance at the skin or mucosal surface to enable data screening correction or invalidation of sensor signals.

After a suitable iontophoretic extraction period, one or both of the sensor electrode sets can be activated in order to detect extracted substances including the analyte of interest. Operation of the iontophoretic sampling device 30 can be controlled by a controller 36 (e.g., a microprocessor), which interfaces with the iontophoretic electrodes, the sensor electrodes, the power supply, the optional temperature and/or conductance sensing elements, a display and other electronics. For example, the controller 36 can include a programmable a controlled circuit source/sink drive for driving the iontophoretic electrodes. Power and reference voltage are provided to the sensor electrodes, and signal amplifiers can be used to process the signal from the working electrode or electrodes. In general, the controller discontinues the iontophoretic current drive during sensing periods. A sensor confidence loop can be provided for continually monitoring the sampling system to insure proper operations.

User control can be carried out using push buttons located on the housing 32, and an optional liquid crystal display (LCD) can provide visual prompts, readouts and visual alarm indications. The microprocessor generally uses a series of program sequences to control the operations of the sampling device, which program sequences can be stored in the microprocessor's read only memory (ROM). Embedded software (firmware) controls activation of measurement and display operations, calibration of analyte readings, setting and display of high and low analyte value alarms, display and setting of time and date functions, alarm time, and display of stored readings. Sensor signals obtained from the sensor electrodes can be processed before storage and display by one or more signal processing functions or algorithms which are stored in the embedded software. The microprocessor can also include an electronically erasable, programmable, read only memory (EEPROM) for storing calibration parameters, user settings and all downloadable sequences. A serial communications port allows the device to communicate with associated electronics, for example, wherein the device is used in a feedback control application to control a pump for delivery of a medicament.

Further, the sampling system can be pre-programmed to begin execution of its signal measurements (or other functions) at a designated time. One application of this feature is to have the sampling system in contact with a subject and to program the sampling system to begin sequence execution during the night so that it is available for calibration immediately upon waking. One advantage of this feature is that it removes any need to wait for the sampling system to warm-up before calibrating it.

2.1.1 Exemplary Embodiments of the Sampling System

An exemplary method and apparatus for sampling small amounts of an analyte via transdermal methods is described below in further detail. The method and apparatus are used to detect and/or quantify the concentration of a target analyte present in a biological system. This sampling is carried out in a continual manner, and quantification is possible even when the target analyte is extracted in sub-millimolar concentrations. Although the method and apparatus are broadly applicable to sampling any chemical analyte and/or substance, the sampling system is expressly exemplified for use in transdermal sampling and quantifying or qualifying glucose or a glucose metabolite.

Accordingly, in one aspect, an automatic sampling system is used to monitor levels of glucose in a biological system. The method can be practiced using a sampling system (device) which transdermally extracts glucose from the system, in this case, an animal subject. Transdermal extraction is carried out by applying an electrical current or ultrasonic radiation to a tissue surface at a collection site. The electrical current or ultrasonic radiation is used to extract small amounts of glucose from the subject into a collection reservoir. The collection reservoir is in contact with a biosensor which provides for measurement of glucose concentration in the subject.

In the practice, a collection reservoir is contacted with a tissue surface, for example, on the stratum corneum of a patient's skin. An electrical or ultrasonic force is then applied to the tissue surface in order to extract glucose from the tissue into the collection reservoir. Extraction is carried out continually over a period of about 1–24 hours, or longer. The collection reservoir is analyzed, at least periodically, to measure glucose concentration therein. The measured value correlates with the subject's blood glucose level.

More particularly, one or more collection reservoirs are placed in contact with a tissue surface on a subject. The collection reservoirs are also contacted with an electrode which generates a current (for reverse iontophoretic extraction) or with a source of ultrasonic radiation such as a transducer (for sonophoretic extraction) sufficient to extract glucose from the tissue into the collection reservoir.

The collection reservoir contains an ionically conductive liquid or liquid-containing medium. The conductive medium is preferably a hydrogel which can contain ionic substances in an amount sufficient to produce high ionic conductivity. The hydrogel is formed from a solid material (solute) which, when combined with water, forms a gel by the formation of a structure which holds water including interconnected cells and/or network structure formed by the solute. The solute may be a naturally occurring material such as the solute of natural gelatin which includes a mixture of proteins obtained by the hydrolysis of collagen by boiling skin, ligaments, tendons and the like. However, the solute or gel forming material is more preferably a polymer material (including, but not limited to, polyethylene oxide, polyvinyl alcohol, polyacrylic acid, polyacrylamidomethylpropanesulfonate and copolymers thereof, and polyvinyl pyrrolidone) present in an amount in the range of more than 0.5% and less than 40% by weight, preferably 8 to 12% by weight when a humectant is also added, and preferably about 15 to 20% by weight when no humectant is added. Additional materials may be added to the hydrogel, including, without limitation, electrolyte (e.g., a salt), buffer, tackifier, humectant, biocides, preservatives and enzyme stabilizers. Suitable hydrogel formulations are described in International Publication Nos. WO 97/02811, published Jan. 30, 1997, and WO 96/00110, published Jan. 4, 1996, each of which publications are incorporated herein by reference in their entireties.

Since the sampling system must be operated at very low (electrochemical) background noise levels, the collection reservoir must contain an ionically conductive medium that does not include significant electrochemically sensitive components and/or contaminants. Thus, the preferred hydrogel composition described hereinabove is formulated using a judicious selection of materials and reagents which do not add significant amounts of electrochemical contaminants to the final composition.

In order to facilitate detection of the analyte, an enzyme is disposed within the one or more collection reservoirs. The enzyme is capable of catalyzing a reaction with the extracted analyte (in this case glucose) to the extent that a product of this reaction can be sensed, e.g., can be detected electrochemically from the generation of a current which current is detectable and proportional to the amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device (see FIG. 1). Glucose oxidase (GOx) is readily available commercially and has well known catalytic characteristics. However, other enzymes can also be used, so long as they specifically catalyze a reaction with an analyte, or derivative thereof (or substance of interest), to generate a detectable product in proportion to the amount of analyte so reacted.

In like manner, a number of other analyte-specific enzyme systems can be used in the sampling system, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

The biosensor electrode must be able to detect the glucose analyte extracted into the one or more collection reservoirs even when present at nominal concentration levels. In this regard, conventional electrochemical detection systems which utilize glucose oxidase (GOx) to specifically convert glucose to hydrogen peroxide, and then detect with an appropriate electrode, are only capable of detecting the analyte when present in a sample in at least mM concentrations. In contrast, the sampling system allows sampling and detection of small amounts of analyte from the subject, wherein the analyte is detected at concentrations on the order of 2 to 4 orders of magnitude lower (e.g., $\mu$M concentration in the reservoir) than presently detectable with conventional systems.

Accordingly, the biosensor electrode must exhibit substantially reduced background current relative to prior such electrodes. In one particularly preferred embodiment, an electrode is provided which contains platinum (Pt) and graphite dispersed within a polymer matrix. The electrode exhibits the following features, each of which are essential to the effective operation of the biosensor: background current in the electrode due to changes in the Pt oxidation state and electrochemically sensitive contaminants in the electrode formulation is substantially reduced; and catalytic activity (e.g., non-electrochemical hydrogen peroxide decomposition) by the Pt in the electrode is reduced.

The Pt-containing electrode is configured to provide a geometric surface area of about 0.1 to 3 $cm^2$, preferably about 0.5 to 2 $cm^2$, and more preferably about 1 $cm^2$. This particular configuration is scaled in proportion to the collection area of the collection reservoir used in the sampling system, throughout which the extracted analyte and/or its reaction products will be present. The electrode is specially formulated to provide a high signal-to-noise ratio (S/N ratio) for this geometric surface area not heretofore available with prior Pt-containing electrodes. For example, a Pt-containing electrode constructed for use in the sampling system and having a geometric area of about 1 $cm^2$ preferably has a background current on the order of about 20 nA or less (when measured with buffer solution at 0.6V), and has high sensitivity (e.g., at least about 60 nA/$\mu$M of $H_2O_2$ in buffer at 0.6V). In like manner, an electrode having a geometric area of about 0.1 $cm^2$ preferably has a background current of about 2 nA or less and sensitivity of at least about 6 nA/$\mu$M of $H_2O_2$; and an electrode having a geometric area of about 3 $cm^2$ preferably has a background current of about 60 nA or less and sensitivity of at least about 180 nA/$\mu$M of $H_2O_2$, both as measured in buffer at 0.6V. These features provide for a high S/N ratio, for example a S/N ratio of about 3 or greater. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times.

The Pt powder used to formulate the electrode composition is also substantially free from impurities, and the Pt/graphite powders are evenly distributed within the polymer matrix using, for example, co-milling or sequential milling of the Pt and graphite. Alternatively, prior to incorporation into the polymer matrix, the Pt can be sputtered onto the graphite powder, colloidal Pt can be precipitated onto the graphite powder (see, e.g., U.K. patent application number GB 2,221,300, published Jan. 31, 1990, and references cited therein), or the Pt can be adsorbed onto the graphite powder to provide an even distribution of Pt in contact with the conductive graphite. In order to improve the S/N ratio of the electrode, the Pt content in the electrode is lower relative to prior Pt or Pt-based electrodes. In a preferred embodiment, the overall Pt content is about 3–7% by weight. Although decreasing the overall amount of Pt may reduce the sensitivity of the electrode, the inventors have found that an even greater reduction in background noise is also achieved, resulting in a net improvement in signal-to-noise quality.

The Pt/graphite matrix is supported by a suitable binder, such as an electrochemically inert polymer or resin binder, which is selected for good adhesion and suitable coating integrity. The binder is also selected for high purity, and for absence of components with electrochemical background. In this manner, no electrochemically sensitive contaminants are introduced into the electrode composition by way of the binder. A large number of suitable such binders are known in the art and are commercially available, including, without limitation, vinyl, acrylic, epoxy, phenoxy and polyester polymers, provided that the binder or binders selected for the formulation are adequately free of electroactive impurities.

The Pt/graphite biosensor electrodes formulated above exhibit reduced catalytic activity (e.g., passive or non-electrochemical hydrogen peroxide degradation) relative to prior Pt-based electrode systems, and thus have substantially improved signal-to-noise quality. In preferred Pt/graphite electrode compositions, the biosensor exhibits about 10–25% passive hydrogen peroxide degradation.

Once formulated, the electrode composition is affixed to a suitable nonconductive surface which may be any rigid or flexible material having appropriate insulating and/or dielectric properties. The electrode composition can be affixed to the surface in any suitable pattern or geometry, and can be applied using various thin film techniques, such as sputtering, evaporation, vapor phase deposition, or the like; or using various thick film techniques, such as film laminating, electroplating, or the like. Alternatively, the composition can be applied using screen printing, pad printing, inkjet methods, transfer roll printing, or similar techniques. Preferably, the electrode is applied using a low temperature screen print onto a polymeric substrate. The screening can be carried out using a suitable mesh, ranging from about 100–400 mesh.

As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted by an associated system controller to provide a glucose concentration value for display. In particular embodiments, the detected current can be correlated with the subject's blood glucose concentration so that the system controller may display the subject's actual blood glucose concentration as measured by the sampling system. For example, the system can be calibrated to the subject's actual blood glucose concentration by sampling the subject's blood during a standard glucose tolerance test, and analyzing the blood glucose using both a standard blood glucose monitor and the sampling system. In this manner, measurements obtained by the sampling system can be correlated to actual values using known statistical techniques.

In one preferred embodiment, the automatic sampling system transdermally extracts the sample in a continual manner over the course of a 1–24 hour period, or longer, using reverse iontophoresis. More particularly, the collection reservoir contains an ionically conductive medium, preferably the hydrogel medium described hereinabove. A first iontophoresis electrode is contacted with the collection reservoir (which is in contact with a target tissue surface), and a second iontophoresis electrode is contacted with either a second collection reservoir in contact with the tissue surface, or some other ionically conductive medium in contact with the tissue. A power source provides an electric potential between the two electrodes to perform reverse iontophoresis in a manner known in the art. As discussed above, the biosensor selected to detect the presence, and possibly the level, of the target analyte (glucose) within a reservoir is also in contact with the reservoir.

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in International Publication No. WO 96/00110, published Jan. 4, 1996.

As an example, to extract glucose, the applied electrical current density on the skin or tissue is preferably in the range of about 0.01 to about 2 $mA/cm^2$. In a preferred embodiment, in order to facilitate the extraction of glucose, electrical energy is applied to the electrodes, and the polarity of the electrodes is alternated at a rate of about one switch every 7.5 minutes (for a 15 minute extraction period), so that each electrode is alternately a cathode or an anode. The polarity switching can be manual or automatic.

Any suitable iontophoretic electrode system can be employed, however it is preferred that a silver/silver chloride (Ag/AgCl) electrode system is used. The iontophoretic electrodes are formulated using two critical performance parameters: (1) the electrodes are capable of continual operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes.

Figure 4:
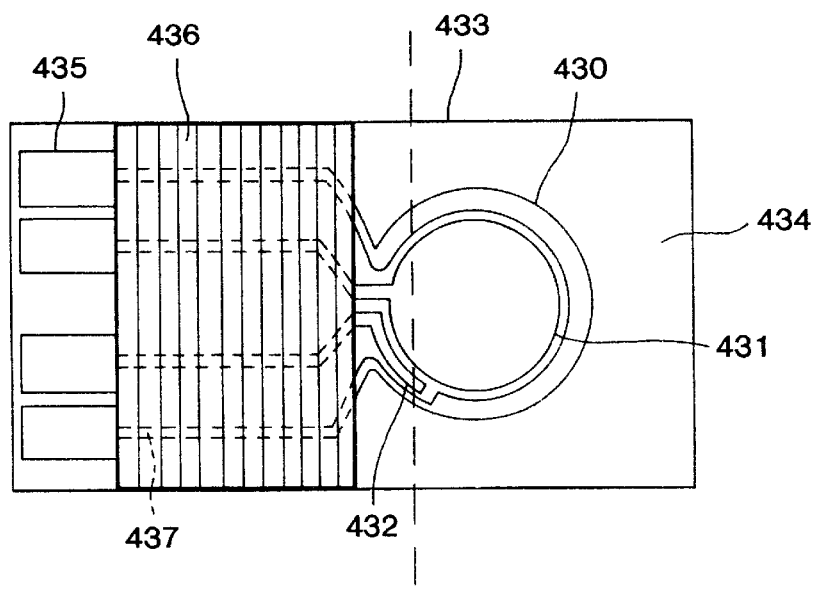
FIG. 4 is a representation of one embodiment of a bimodal electrode design. The figure presents an overhead and schematic view of the electrode assembly 433. In the figure, the bimodal electrode is shown at 430 and can be, for example, a Ag/AgCl iontophoretic/counter electrode. The sensing or working electrode (made from, for example, platinum) is shown at 431. The reference electrode is shown at 432 and can be, for example, a Ag/AgCl electrode. The components are mounted on a suitable nonconductive substrate 434, for example, plastic or ceramic. The conductive leads 437 (represented by dotted lines) leading to the connection pad 435 are covered by a second nonconductive piece 436 (the area represented by vertical striping) of similar or different material (e.g., plastic or ceramic). In this example of such an electrode the working electrode area is approximately 1.35 $cm^2$. The dashed line in FIG. 4 represents the plane of the cross-sectional schematic view presented in FIG. 5.
Figure 5:
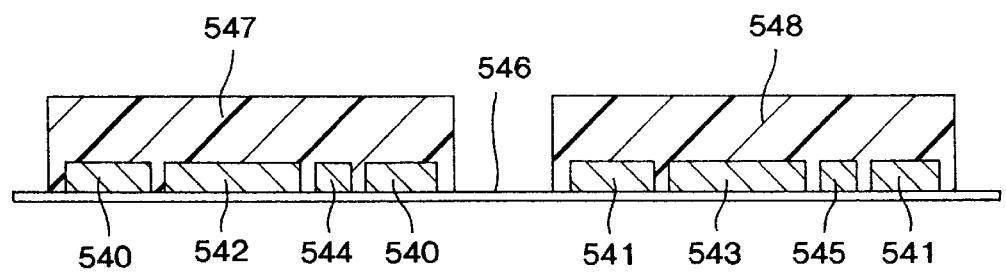
FIG. 5 is a representation of a cross-sectional schematic view of the bimodal electrodes as they may be used in conjunction with a reference electrode and a hydrogel pad. In the figure, the components are as follows: bimodal electrodes 540 and 541; sensing electrodes 542 and 543; reference electrodes 544 and 545; a substrate 546; and hydrogel pads 547 and 548.

In an alternative embodiment, the sampling device can operate in an alternating polarity mode necessitating the presence of a first and second bimodal electrodes (FIG. 5, 540 and 541) and two collection reservoirs (FIG. 5, 547 and 548). Each bi-modal electrode (FIG. 4, 430; FIG. 5, 540 and 541) serves two functions depending on the phase of the operation: (1) an electro-osmotic electrode (or iontophoretic electrode) used to electrically draw analyte from a source into a collection reservoir comprising water and an electrolyte, and to the area of the electrode subassembly; and (2) as a counter electrode to the first sensing electrode at which the chemical compound is catalytically converted at the face of the sensing electrode to produce an electrical signal.

The reference (FIG. 5, 544 and 545; FIG. 4, 432) and sensing electrodes (FIG. 5, 542 and 543; FIG. 4, 431), as well as, the bimodal electrode (FIG. 5, 540 and 541; FIG. 4, 430) are connected to a standard potentiostat circuit during sensing. In general, practical limitations of the system require that the bimodal electrode will not act as both a counter and iontophoretic electrode simultaneously.

The general operation of an iontophoretic sampling system is the cyclical repetition of two phases: (1) a reverse-iontophoretic phase, followed by a (2) sensing phase. During the reverse iontophoretic phase, the first bimodal electrode (FIG. 5, 540) acts as an iontophoretic cathode and the second bimodal electrode (FIG. 5, 541) acts as an iontophoretic anode to complete the circuit. Analyte is collected in the reservoirs, for example, a hydrogel (FIG. 5, 547 and 548). At the end of the reverse iontophoretic phase, the iontophoretic current is turned off. During the sensing phase, in the case of glucose, a potential is applied between the reference electrode (FIG. 5, 544) and the sensing electrode (FIG. 5, 542). The chemical signal reacts catalytically on the catalytic face of the first sensing electrode (FIG. 5, 542) producing an electrical current, while the first bi-modal electrode (FIG. 5, 540) acts as a counter electrode to complete the electrical circuit.

At the end of the sensing phase, the next iontophoresis phase begins. The polarity of the iontophoresis current is reversed in this cycle relative to the previous cycle, so that the first bi-modal electrode (FIG. 5, 540) acts as an iontophoretic anode and the second bi-modal electrode (FIG. 5, 541) acts as an iontophoretic cathode to complete the circuit. At the end of the iontophoretic phase, the sensor is activated. The chemical signal reacts catalytically on the catalytic face of the second sensing electrode (FIG. 5, 543) producing an electrical current, while the second bi-modal electrode (FIG. 5, 541) acts as a counter electrode to complete the electrical circuit.

The iontophoretic and sensing phases repeat cyclically with the polarity of the iontophoretic current alternating between each cycle. This results in pairs of readings for the signal, that is, one signal obtained from a first iontophoretic and sensing phase and a second signal obtained from the second phase. These two values can be used (i) independently as two signals, (ii) as a cumulative (additive) signal, or (iii) the signal values can be added and averaged.

If two active reservoirs are used for analyte detection (for example, where both hydrogels contain the GOx enzyme), a sensor consistency check can be employed that detects whether the signals from the reservoirs are changing in concert with one another. This check compares the percentage change from the calibration signal for each reservoir, then calculates the difference in percentage change of the signal between the two reservoirs. If this difference is greater than a predetermined threshold value (which is commonly empirically determined), then the signals are said not to be tracking one another and the data point related to the two signals can be, for example, ignored.

The electrode described is particularly adapted for use in conjunction with a hydrogel collection reservoir system for monitoring glucose levels in a subject through the reaction of collected glucose with the enzyme glucose oxidase present in the hydrogel matrix.

The bi-modal electrode is preferably comprised of Ag/AgCl. The electrochemical reaction which occurs at the surface of this electrode serves as a facile source or sink for electrical current. This property is especially important for the iontophoresis function of the electrode. Lacking this reaction, the iontophoresis current could cause the hydrolysis of water to occur at the iontophoresis electrodes causing pH changes and possible gas bubble formation. The pH changes to acidic or basic pH could cause skin irritation or burns. The ability of an Ag/AgCl electrode to easily act as a source of sink current is also an advantage for its counter electrode function. For a three electrode electrochemical cell to function properly, the current generation capacity of the counter electrode must not limit the speed of the reaction at the sensing electrode. In the case of a large sensing electrode, the ability of the counter electrode to source proportionately larger currents is required.

The design of the sampling system provides for a larger sensing electrode (see for example, FIG. 4) than previously designed. Consequently, the size of the bimodal electrode must be sufficient so that when acting as a counter electrode with respect to the sensing electrode the counter electrode does not become limiting the rate of catalytic reaction at the sensing electrode catalytic surface.

Two methods exist to ensure that the counter electrode does not limit the current at the sensing electrode: (1) the bi-modal electrode is made much larger than the sensing electrode, or (2) a facile counter reaction is provided.

During the reverse iontophoretic phase, the power source provides a current flow to the first bi-modal electrode to facilitate the extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode sub-assembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present sampling system, the electrical current measured at the sensing electrode subassembly is the current that is correlated with an amount of chemical signal.

With regard to continual operation for extended periods of time, Ag/AgCl electrodes are provided herein which are capable of repeatedly forming a reversible couple which operates without unwanted electrochemical side reactions (which could give rise to changes in pH, and liberation of hydrogen and oxygen due to water hydrolysis). The Ag/AgCl electrodes of the present sampling system are thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also formulated using analytical- or electronic-grade reagents and solvents, and the polymer binder composition is selected to be free of electrochemically active contaminants which could diffuse to the biosensor to produce a background current.

Since the Ag/AgCl iontophoretic electrodes must be capable of continual cycling over extended periods of time, the absolute amounts of Ag and AgCl available in the electrodes, and the overall Ag/AgCl availability ratio, can be adjusted to provide for the passage of high amounts of charge. Although not limiting in the sampling system described herein, the Ag/AgCl ratio can approach unity. In order to operate within the preferred system which uses a biosensor having a geometric area of 0.1 to 3 $cm^2$, the iontophoretic electrodes are configured to provide an approximate electrode area of 0.3 to 1.0 $cm^2$, preferably about 0.85 $cm^2$. These electrodes provide for reproducible, repeated cycles of charge passage at current densities ranging from about 0.01 to 1.0 $mA/cm^2$ of electrode area. More particularly, electrodes constructed according to the above formulation parameters, and having an approximate electrode area of 0.85 $cm^2$, are capable of a reproducible total charge passage (in both anodic and cathodic directions) of 270 mC, at a current of about 0.3 mA (current density of 0.35 $mA/cm^2$) for 48 cycles in a 24 hour period.

Once formulated, the Ag/AgCl electrode composition is affixed to a suitable rigid or flexible nonconductive surface as described above with respect to the biosensor electrode composition. A silver (Ag) underlayer is first applied to the surface in order to provide uniform conduction. The Ag/AgCl electrode composition is then applied over the Ag underlayer in any suitable pattern or geometry using various thin film techniques, such as sputtering, evaporation, vapor phase deposition, or the like, or using various thick film techniques, such as film laminating, electroplating, or the like. Alternatively, the Ag/AgCl composition can be applied using screen printing, pad printing, inkjet methods, transfer roll printing, or similar techniques. Preferably, both the Ag underlayer and the Ag/AgCl electrode are applied using a low temperature screen print onto a polymeric substrate. This low temperature screen print can be carried out at about 125 to 160° C., and the screening can be carried out using a suitable mesh, ranging from about 100–400 mesh.

In another preferred embodiment, the automatic sampling system transdermally extracts the sample in a continual manner over the course of a 1–24 hour period, or longer, using sonophoresis. More particularly, a source of ultrasonic radiation is coupled to the collection reservoir and used to provide sufficient perturbation of the target tissue surface to allow passage of the analyte (glucose) across the tissue surface. The source of ultrasonic radiation provides ultrasound frequencies of greater than about 10 MHz, preferably in the range of about 10 to 50 MHz, most preferably in the range of about 15 to 25 MHz. It should be emphasized that these ranges are intended to be merely illustrative of the preferred embodiment; in some cases higher or lower frequencies may be used.

The ultrasound may be pulsed or continuous, but is preferably continuous when lower frequencies are used. At very high frequencies, pulsed application will generally be preferred so as to enable dissipation of generated heat. The preferred intensity of the applied ultrasound is less than about 5.0 W/cm$^2$, more preferably is in the range of about 0.01 to 5.0 W/cm$^2$, and most preferably is in the range of 0.05 to 3.0 W/cm$^2$.

Virtually any type of device may be used to administer the ultrasound, providing that the device is capable of producing the suitable frequency ultrasonic waves required by the sampling system. An ultrasound device will typically have a power source such as a small battery, a transducer, and a means to attach the system to the sampling system collection reservoir. Suitable sonophoresis sampling systems are described in International Publication No. WO 91/12772, published Sep. 5, 1991, the disclosure of which is incorporated herein by reference.

As ultrasound does not transmit well in air, a liquid medium is generally needed in the collection reservoir to efficiently and rapidly transmit ultrasound between the ultrasound applicator and the tissue surface.

Figure 3:
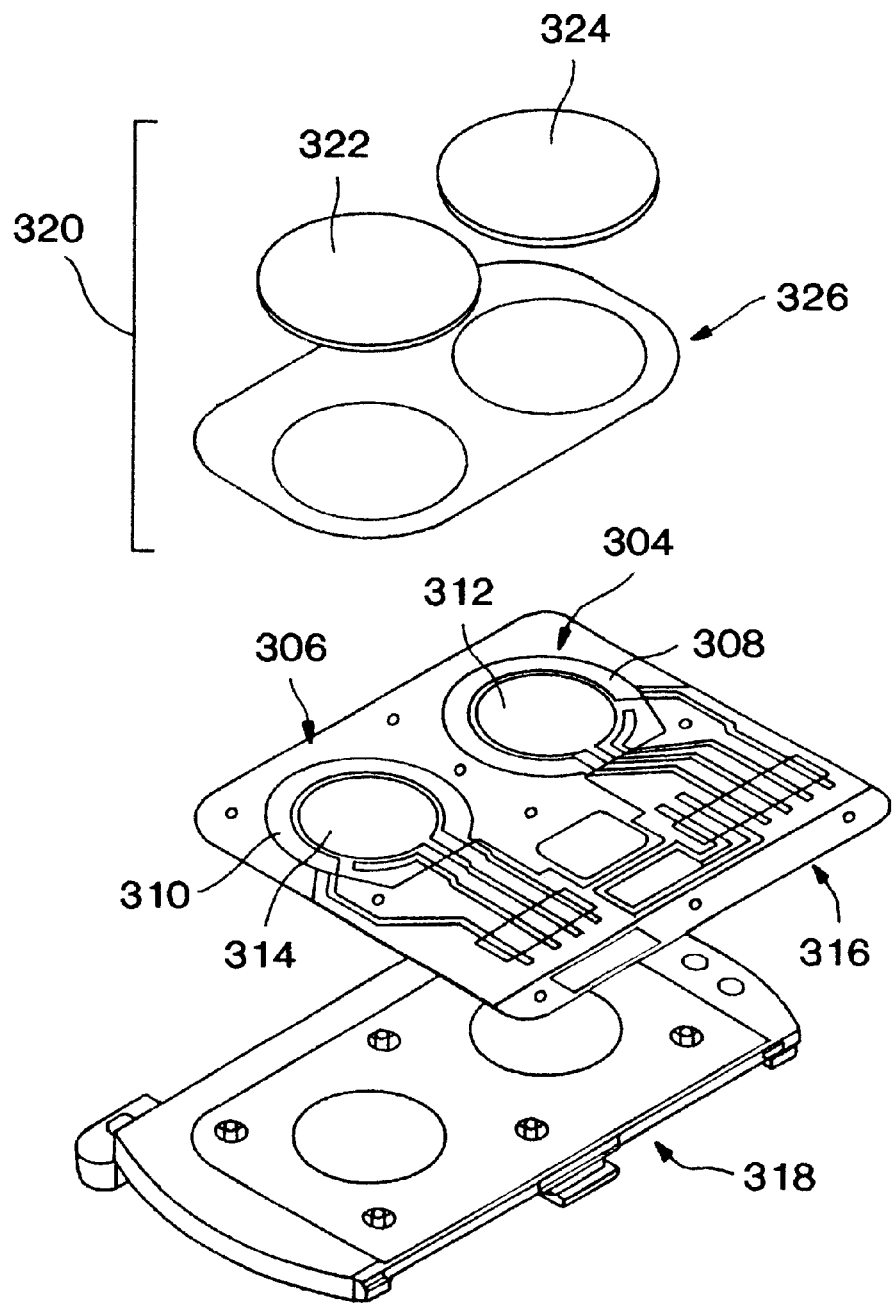
FIG. 3 is an exploded pictorial representation of components from a preferred embodiment of the automatic sampling system of the present invention.

Referring now to FIG. 3, an exploded view of the key components from a preferred embodiment of an autosensor is presented. The sampling system components include two biosensor/iontophoretic electrode assemblies, 304 and 306, each of which have an annular iontophoretic electrode, respectively indicated at 308 and 310, which encircles a biosensor 312 and 314. The electrode assemblies 304 and 306 are printed onto a polymeric substrate 316 which is maintained within a sensor tray 318. A collection reservoir assembly 320 is arranged over the electrode assemblies, wherein the collection reservoir assembly comprises two hydrogel inserts 322 and 324 retained by a gel retaining layer 326.

Figure 9:
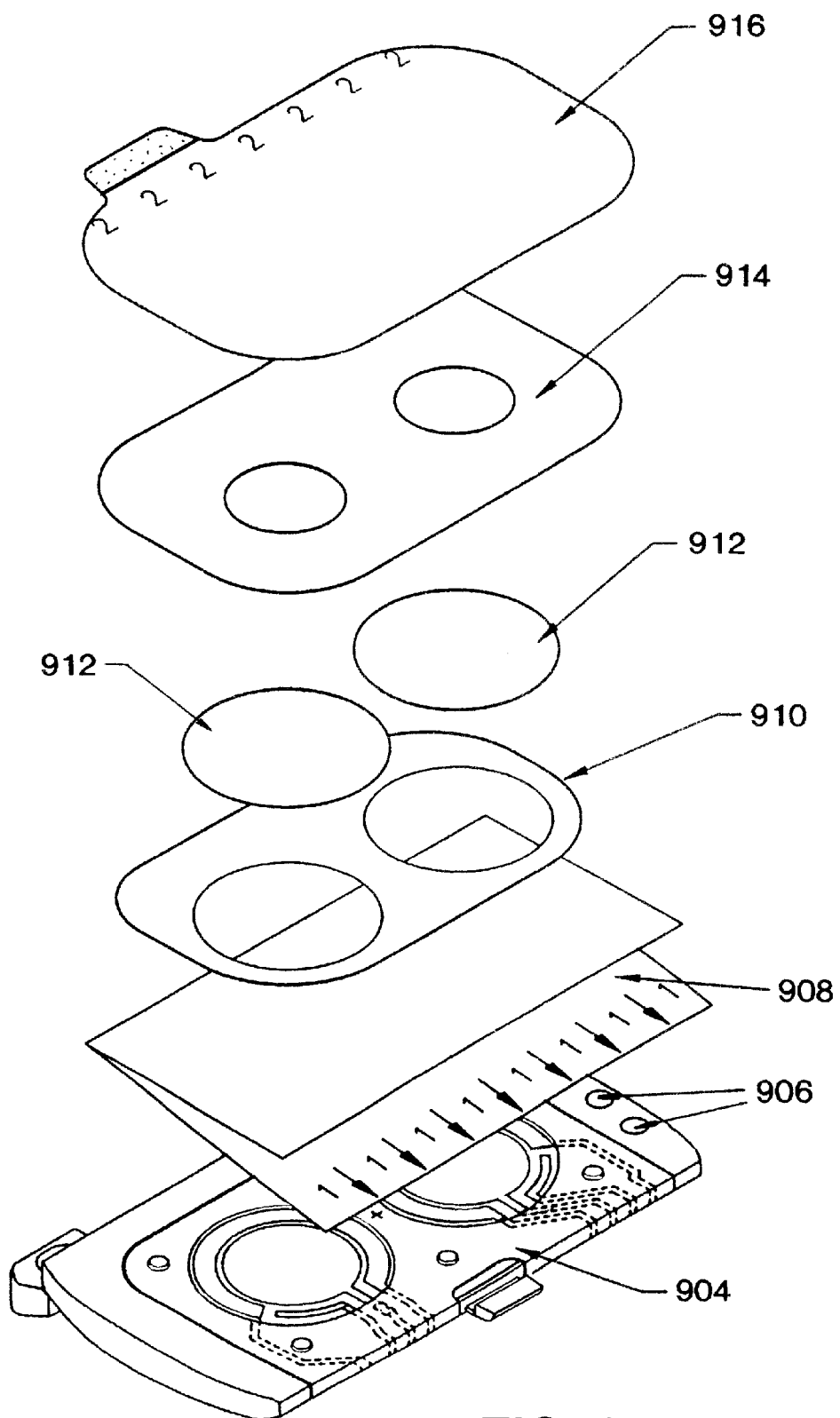
FIG. 9 depicts an exploded view of an embodiment of an autosensor.

Referring now to FIG. 9, an exploded view of the key components from another embodiment of an autosensor for use in an iontophoretic sampling device is presented. The sampling system components include, but are not limited to, the following: a sensor-to-tray assembly comprising two bimodal electrode assemblies and a support tray 904; two holes 906 to insure proper alignment of the support tray in the sampling device; a plowfold liner 908 used to separate the sensors from the hydrogels 912 (for example, during storage); a gel retaining layer 910; a mask layer 914 (where the gel retaining layer, hydrogels, and mask layer form a collection assembly, which can, for example, be a laminate); and a patient liner 916.

The components shown in exploded view in FIGS. 3 and 9 are intended for use in, for example, an automatic sampling device which is configured to be worn like an ordinary wristwatch. As described in International Publication No. WO 96/00110, published Jan. 4, 1996, the wristwatch housing (not shown) contains conductive leads which communicate with the iontophoretic electrodes and the biosensor electrodes to control cycling and provide power to the iontophoretic electrodes, and to detect electrochemical signals produced at the biosensor electrode surfaces. The wristwatch housing can further include suitable electronics (e.g., microprocessor, memory, display and other circuit components) and power sources for operating the automatic sampling system.

Modifications and additions to the embodiments of FIGS. 3 and 9 will be apparent to those skilled in the art in light of the teachings of the present specification. The laminates and collection assemblies described herein are suitable for use as consumable components in an iontophoretic sampling device.

In one aspect, the electrode assemblies can include bimodal electrodes as shown in FIG. 4 and described above.

Modifications and additions to the embodiments shown in FIGS. 3 and 9 will be apparent to those skilled in the art.

2.2.0 Converting to an Analyte-Specific Value

The raw signal is then converted into an analyte-specific value using a calibration step which correlates the signal obtained from the sensing device with the concentration of the analyte present in the biological system. A wide variety of calibration techniques can be used to interpret such signals. These calibration techniques apply mathematical, statistical and/or pattern recognition techniques to the problem of signal processing in chemical analyses, for example, using neural networks, genetic algorithm signal processing, linear regression, multiple-linear regression, or principal components analysis of statistical (test) measurements.

One method of calibration involves estimation techniques. To calibrate an instrument using estimation techniques, it is necessary to have a set of exemplary measurements with known concentrations referred to as the calibration set (e.g., reference set). This set consists of S samples, each with m instrument variables contained in an S by m matrix (X), and an S by 1 vector (y), containing the concentrations. If a priori information indicates the relationship between the measurement and concentration is linear, the calibration will attempt to determine an S by 1 transformation or mapping (b), such that y=Xb, is an optimal estimate of y according to a predefined criteria. Numerous suitable estimation techniques useful in the practice of the invention are known in the art. These techniques can be used to provide correlation factors (e.g., constants), which correlation factors are then used in a mathematical transformation to obtain a measurement value indicative of the concentration of analyte present in the biological system at the times of measurement.

In one particular embodiment, the calibration step can be carried out using artificial neural networks or genetic algorithms. The structure of a particular neural network algorithm used in the practice of the invention can vary widely; however, the network should contain an input layer, one or more hidden layers, and one output layer. Such networks can be trained on a test data set, and then applied to a population. There are an infinite number of suitable network types, transfer functions, training criteria, testing and application methods which will occur to the ordinarily skilled artisan upon reading the instant specification.

The iontophoretic glucose sampling device described hereinabove typically uses one or more "active" collection reservoirs (e.g., each containing the GOx enzyme) to obtain measurements. In one embodiment, two active collection reservoirs are used. An input value can be obtained from these reservoirs by, for example, taking an average between signals from the reservoirs for each measurement time point or using a summed value. Such inputs are discussed in greater detail below. In another embodiment, a second collection reservoir can be provided which does not contain, for example, the GOx enzyme. This second reservoir can serve as an internal reference (blank) for the sensing device, where a biosensor is used to measure the "blank" signal from the reference reservoir which signal can then be used in, for example, a blank subtraction step.

In the context of such a sampling device an algorithm, in a preferred embodiment a Mixtures of Experts algorithm, could use the following inputs to provide a blood glucose measurement: time (for example, time since monitor was applied to a subject, and/or time since calibration); signal from an active reservoir; signal from a blank reservoir; averaged (or a cumulative) signal from two active reservoirs; calibration time; skin temperature; voltage; normalized background; raw data current; peak or minimum value of a selected input, e.g., current, averged signal, calibrated signal; discrete value points of a selected input, e.g., current, averged signal, calibrated signal; integral avgerage temperature, initial temperature, or any discrete time temperature; skin conductivity, including, but not limited to, sweat value, iontophoretic voltage, baseline value, normalized baseline value, other background values; relative change in biosensor current or iontophoretic voltage (relative to calibration) as an indicator of decay; alternate integration ranges for calculating nanocoulomb (nC) values, e.g., using an entire biosensor time interval, or alternative ranges of integration (for example, using discrete time points instead of ranges, break out intervals from the total sampling time interval, or full integration of the interval plus partial integration of selected portions of the interval); and, when operating in the training mode, measured glucose (use of exemplary inputs are presented in Examples 1 and 2). Further, a calibration ratio check is described in Example 4 that is useful to insure that the calibration has been efficacious, and that the calibration demonstrates a desired level of sensitivity of the sampling system.

2.3.0 Predicting Measurements

The analyte-specific values obtained using the above techniques are used herein to predict target analyte concentrations in a biological system using a Mixtures of Experts (MOE) analysis.

The Mixtures of Experts algorithm breaks up a non-linear prediction equation into several linear prediction equations ("Experts"). An "Expert" routine is then used to switch between the different linear equations. In the equations presented below, the w (weighting) factor determines the switch by weighting the different Experts with a number between 0 and 1, with the restriction that:

$$\sum_{i=1}^{n} w_i = 1$$

The Mixtures of Experts algorithm of the present invention is based on the ideal case presented in Equation 1, where the individual experts have a linear form:

$$An = \sum_{i=1}^{n} An_i w_i \qquad (1)$$

wherein (An) is an analyte of interest, n is the number of experts, $An_i$ is the analyte predicted by Expert i; and $w_i$ is a parameter. The number of experts is chosen based on the quality of the fit of the model, subject to the requirement that it is desirable to use the least number of experts possible. The number of experts is preferably less than 100, and more preferably less than 30. In most cases, selection of the fewest possible experts is desirable.

The individual Experts $An_i$ are further defined by the expression shown as Equation (2).

$$An_i = \sum_{j=1}^{m} a_{ij} p_j + z_i \qquad (2)$$

wherein, $An_i$ is the analyte predicted by Expert i; $P_j$ is one of m parameters, m is typically less than 100; $a_{ij}$ are coefficients; and $z_i$ is a constant.

The weighting value, $w_i$, is defined by the formula shown as Equation (3).

$$w_i = \frac{e^{d_i}}{\left[\sum_{k=1}^{n} e^{d_k}\right]} \qquad (3)$$

where e refers to the exponential function and the $d_k$ (note that the $d_i$ in the numerator of Equation 3 is one of the $d_k$) are a parameter set analogous to Equation 2 that is used to determine the weights $w_i$. The $d_k$ are given by Equation 4.

$$d_k = \sum_{j=1}^{m} \alpha_{jk} P_j + \omega_k \qquad (4)$$

where $\alpha_{jk}$ is a coefficient, $P_j$ is one of m parameters, and where $\omega_k$ is a constant.

The Mixtures of Experts method described by the above equations is supplied with a large data base of empirically obtained information about the parameters defined by the equations. By employing a linear regression function, the equations are simultaneously solved for the values of all coefficients and constants. In other words, the algorithm is trained to be predictive for the value of An (the analyte) given a particular set of data. A preferred optimization method to determine the coefficients and constants is the Expectation Maximization method (Dempster, A. P., N. M. Laird, and D. B. Rubin, *J. Royal Statistical Society* (Series B-Methodological) 39:(1), 1977). Other optimization methods include the Levenburg-Marquardt algorithm (Marquardt, D. W., *J. Soc. Ind. Appl. Math.* 11:p431–441, 1963) and the Simplex algorithm (Nelder, J. A., and Mead, R., *Computer Journal* 7:p308, 1965).

In the context of blood glucose monitoring with an iontophoretic sampling device, the MOE algorithm allows for the accurate prediction of glucose concentration. In this regard, during a typical iontophoretic measuring cycle, iontophoretic extraction of the analyte is carried out for a suitable amount of time, for example about 1 to 30 minutes, after which time the extracted analyte is detected for a suitable amount of time, for example about 1–30 minutes. An application of the Mixtures of Experts algorithm to a specific set of parameters for glucose monitoring is presented in Example 1.

In the context of blood glucose monitoring with an iontophoretic sampling device, the Mixtures of Experts algorithm allows for the accurate prediction of blood glucose concentrations.

2.4.0 Algorithm Modifications

A further aspect of the present invention is the modification of the Mixtures of Experts (MOE) algorithm. The MOE can be modified in a number of ways including, but not limited to, the following modifications: using different groups of selected inputs (see above); adapting the algorithm by modifying the training set; using different algorithms or modifications of the MOE for different ranges of analyte detection; using different statistical distributions in the Mixtures of Experts; rejection of selected expert(s); and, switching algorithms.

2.4.1 Adapting the Algorithm

The Mixtures of Experts (MOE) is trained using sets of data that contain patterns. Those patterns, represented in a training data set, typically give good performance. Accordingly, training MOE with a wide variety of patterns improves the predictive performance of MOE, for example, using a variety of blood glucose patterns that occur in diabetics patients to obtain parameters that represent the patterns. In this case the selected patterns are used to develop an appropriate training set for MOE and then the parameters generated from that training set are used to test data representing a variety of patterns. In one embodiment, a "global" training set may be augmented by providing a training data set developed from an individual subject's blood glucose data taken over several (or many) days. Such an individual pattern is potentially useful to customize the algorithm to that subject. The parameters generated from using a training set including such an individual patterns is then tested in the same individual to determine whether the expanded training data set provides better predicted values. In an alternative embodiment, a selected percentage of the global training set can be used with the individual's training set (rather than using the entire global training set).

Further, the data comprising a training data set can be specifically chosen to optimize performance of the MOE under specific conditions. Such optimization may include, for example, using diverse data sets or selecting the best data to represent a specific condition. For example, different training data sets based on data obtained from a variety of races can be used to train the MOE to optimize predictive performance for individual members of the different races represented by different data sets.

Finally, MOE is typically trained with values chosen in a selected range (e.g., blood glucose values in the range of 40–400 mg/dl). However, the MOE can be trained with data sets that fall outside of the selected range.

2.4.2 Algorithm Optimized for Different Ranges

The MOE can be optimized for predictive performance in selected ranges of data. Depending on the range different MOEs may be invoked for prediction of analyte values (see "Switching Algorithms" below). Alternatively, different algorithms can be used for prediction of values in selected ranges of analyte detection. For example, MOE may be used for prediction of glucose values in a range of 40–400 mg/dl; however, at low and high ends of glucose values a specifically defined function can be applied to the data in order to get preferred values. Such preferred values may, for example, be useful in the situation where under-prediction is more desirable than over-prediction (e.g., at low blood glucose values). In this case a modification of MOE may be used or an specific algorithm may be optimized for prediction in the selected range using, for example, a non-linear distribution function that emphasizes predicting low blood glucose (BG) in the range $BG \leq 100$.

2.4.3 Employing Different Distribution Functions

When calculating the weights used in the MOE algorithm a selected distribution is used. One exemplary distribution is a Gaussian distribution (Example 3) that weighs deviations relative to the square of difference from the mean. However, other distributions can be used to improve predictive function of the algorithm. For example, a Laplacian distribution function was used in the calculations presented in Example 4. The Laplacian distribution has longer tails than a Gaussian distribution, and weighs deviations relative to the absolute difference from the mean. Other distribution functions can be used as well including, but not limited to, Cauchy distribution or a specific distribution function devised (or calculated) based on specific data sets obtained, for example, from different individuals or different groups of individuals (e.g., different races).

2.4.4 Rejecting Experts

When multiple experts are used in the MOE each expert can be inspected to determine if, for example, one or more of the experts is providing incongruous values. When such an expert is identified (e.g., in the calculation of a particular data point) the expert may be eliminated for that calculation and the weights of the remaining experts readjusted appropriately. Inspection of the experts can be carried out by a separate algorithm and can, for example, be based on whether the value predicted by the expert falls outside of a designated range. If the value falls outside of a designated range, the expert may be eliminated in that calculation. For example, Example 3 describes the use of three experts ($BG_1$, $BG_2$, and $BG_3$) in an MOE for prediction of blood glucose values, wherein a weighted average is used to calculate the final blood glucose value. However, each of these three experts can be inspected to determine if one (or more) of them does not make sense (e.g., is providing a stochastic or out-lying value significantly different from the other two experts). The expert providing the incongruous value is disregarded and the weights of the other two experts are readjusted accordingly.

2.4.5 Switching Algorithms

In yet another aspect of the present invention, prediction of the concentration of an analyte can be accomplished using specialized algorithms, where the specialized algorithms are useful for predictions in particular situations (e.g., particular data sets or ranges of predicted values) and where the algorithm used for performing the calculations is determined based on the situation. In this case a "switch" can be used to employ one (or more) algorithm rather than another (or more) algorithm. For example, a global MOE algorithm can be the switch used to selected one of three different MOE algorithms. In one embodiment such a global MOE algorithm may be used to determine a blood glucose value. The blood glucose value is determined, by the algorithm, to fall into one of three ranges (for example, low, normal, and high). For each range there is an separate MOE algorithm that optimizes the prediction for values in the particular range. The global MOE algorithm then selects the appropriate MOE algorithm based on the value and the selected MOE performs a new prediction of blood glucose values based on the original input values but optimized for the range into which the value was predicted (by the global MOE) to fall. As a further illustration, inputs to determine a blood glucose value are provided to a global MOE which determines that the value is a low-value. The inputs are then directed to a Low-Value Optimized MOE to generate a more accurate predicted blood glucose value.

Specialized algorithms may be developed to be used in different parts of a range of analyte signal spectrum or other input values (e.g., high signal/low signal; high BGCal/low BGCal; high/low calratio; high/low temp; etc., for all variables used in the prediction). A global algorithm can be used to decide which region of the spectrum the analyte signal is in, and then the global algorithm switches the data to the appropriate specialized algorithm.

In another embodiment, an algorithm other than the MOE can be used as the switch to choose among a set of MOE algorithms, or an MOE can be used as the switch to choose among a set of other algorithms. Further, there can be multiple levels of specialized switching (which can be graphically represented for instance by branched tree-diagrams).

Following here are several specific, non-limiting examples, of the uses of switching in the practice of the present invention when blood glucose values are being determined.

In one embodiment, variables are identified that explicitly represent signal decay, for example, a switch based on elapsed time since calibration (early or late) or the value of Calratio at CAL (high or low). An exemplary switch of this type is represented by elapsed time since calibration where, for example, the algorithm described in Example 3 may be trained independently with inputs from an early phase of sensor use and inputs from a late phase sensor use (e.g., the total useful life of a sensor element may be split into two halves—early and late). Then, depending on the time since calibration that selected input values are being obtained (an exemplary switch), the input values are directed to an MOE algorithm that was trained on data from the appropriate phase (i.e., either early or late). Such a switch is useful to help correct for error based in sensor decay.

Another exemplary switch of this type is represented by the value of Calratio at the calibration point. Calratio is described in Example 4. The Calratio is a measure of sensor sensitivity. Accordingly, if desired the Calratio range can be divided into two halves (high and low ranges). The algorithm described in Example 3 may be trained independently with inputs from the high and low ranges of the Calratio. A switch is then based on the Calratio values to direct the inputs to the MOE algorithm that is trained with the appropriate data set (i.e., data sets corresponding to inputs from high and low Calratio ranges).

2.5.0 Decreasing the Bias of a Data Set

In addition to the MOE algorithm described in the present specification, following here is a description of a method to alter data used to generate a training data set so as to correct slope, intercept (and resultant bias) introduced by the limited range of data input. This invention provides a useful correction for any asymmetric data input that gives a bias to resultant predictions. In this method, the values of a data set are used to create a second data set that mirrors the first, i.e., positive values become negative values (opposite signs). The two data sets are then used as the training data set. This transformation of the asymmetrical data set results in a forced symmetry of the data comprising the training set.

Figure 10A:
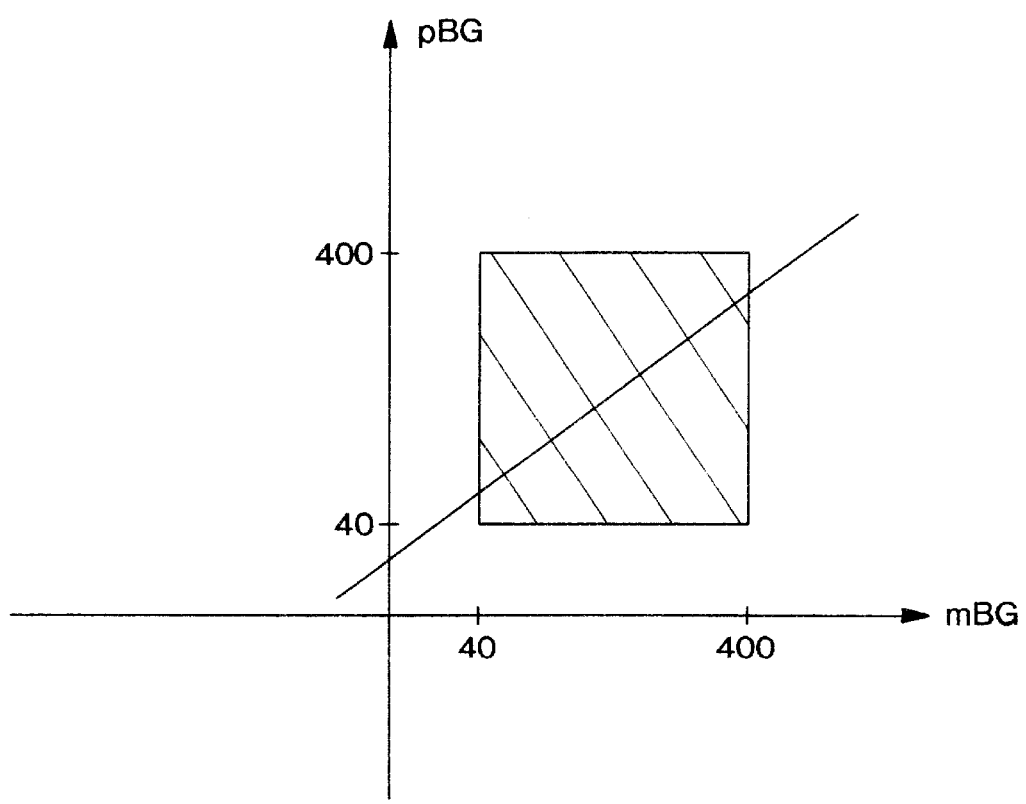
FIGS. 10A and 10B graphically illustrate the method of the present invention used for decreasing the bias of a data set.

The following is a non-limiting example of this method for the correction of bias using blood glucose level determination. In the blood glucose value determinations described herein there is an inherent bias (manifested by a slope of <1 and a positive intercept, e.g., FIG. 10A; in the figure, pBG is predicted blood glucose and mBG is directly measured blood glucose—measured, for example, using a HemoCue® meter) introduced into the prediction function. This is in part due to the fact that there are no blood glucose levels of <40 mg/dl used in the data input training set. The data input for training the MOE algorithm, used to predict blood glucose levels, uses, for example, the following variables: elapsed time since calibration, average signal, calibrated signal, and the blood glucose at the calibration point (see, e.g., Examples 3 and 4). The value that these inputs predict and try to match is directly measured blood glucose. The allowed range for blood glucose is 40–400 mg/dl. Due to this limited range of blood glucose, the resultant function predictions (i.e., via the MOE) result in an inherent bias, slope <1 and positive intercept when plotting predicted blood glucose (y-axis variable, pBG, FIG. 10A) versus directly measured blood glucose (x-axis variable, mBG, FIG. 10A).

Figure 10B:
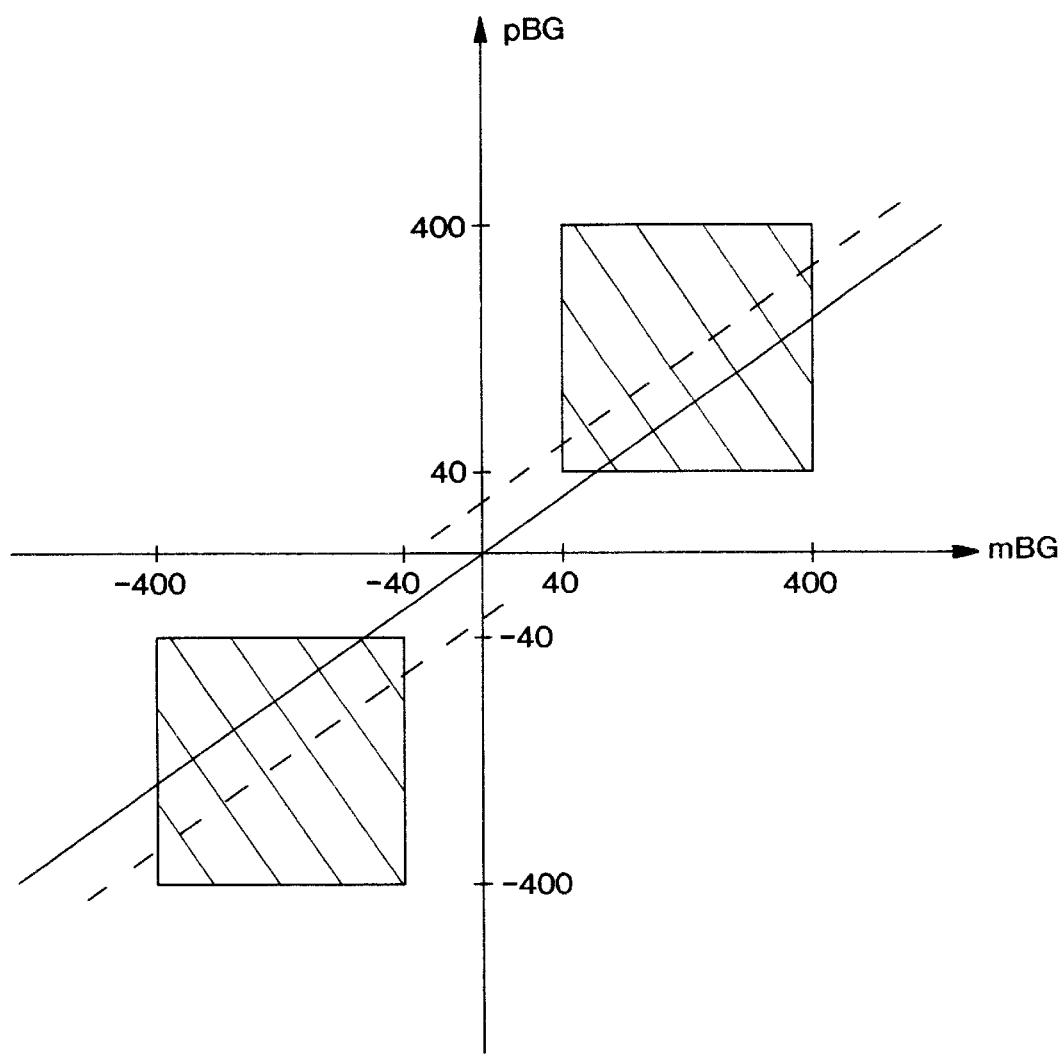

The method of the present invention circumvents this problem by augmenting the original input data set with a data set comprising the same elapsed time since calibration, but with values of the average signal (in nanocoulombs) and directly measured blood glucose both of the opposite sign relative to the original, real data set. The calibrated signal is then calculated using the opposite sign data. In this way the input data is doubled and is now symmetric around the origin (FIG. 10B; in the figure, pBG is predicted blood glucose and mBG is directly measured blood glucose—measured, for example, using a HemoCue® meter). In FIG. 10B the dotted lines represent the slopes predicted from the single data set with which they are associated. The solid line between the two dashed lines represents the corrected slope based on use of the original data set and the opposite sign data set to train the algorithm.

The value of this approach when plotting predicted blood glucose(using MOE) versus measured blood glucose can be seen by examining the results presented in the following table.

|  | Original Data Set | Original Data Set & Opposite Sign Data Set |
| --- | --- | --- |
| Deming Slope* | 0.932 | 1.042 |
| Deming Intercept* | 12.04 | −5.63 |
| Bias 50 mg/dl | 8.64 | −3.53 |
| Bias 80 mg/dl | 6.6 | −2.27 |
| Bias 100 mg/dl | 5.24 | −1.43 |
| Bias 150 mg/dl | 1.84 | 0.67 |
| Bias 200 mg/dl | −1.56 | 2.77 |

*Based on orthogonal regression with a variance ratio equal to two.

As the results in this table demonstrate, the bias reducing method of the present invention has a slope closer to 1, an intercept closer to zero, and the bias values are, in general, closer to zero.

Accordingly, one aspect of the present invention is a method for decreasing the bias of a data set. The method involves generating a second data set that has values opposite in sign of the original data set and using this first and second data set as a combined data set to train the algorithm (e.g., MOE).

EXAMPLES

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Application of the "Mixtures of Experts" to Glucose Monitoring

This example describes the use of a Mixtures of Experts (MOE) algorithm to predict blood glucose data from a series of signals.

In the present example, a GlucoWatch® monitor was used to collect data and the following variables were chosen to generate data sets for the MOE algorithm:

1) elapsed time (time), elapsed time since the GlucoWatch® monitor was applied to the subject, i.e., elapsed time since the sampling system was placed in operative contact with the biological system;

2) active signal (active), in this example, the value of the active parameter corresponded to the nanoamp signal that was integrated over the sensing time-interval to give the active parameter in nanocoulombs (nC);

3) calibrated signal (signal), in this example was obtained by multiplying an active by a constant, where the constant was defined as the blood glucose level at the calibration point divided by the active value at the is calibration point. For example, as follows:

$$signal = \frac{BG/cp}{active/cp}(active)$$

where the slope of the line active versus blood glucose had a non-zero intercept and the offset took into account that the intercept was not zero. In the alternative, the constant could be as follows:

$$signal = \frac{BG/cp}{(active/cp + offset)}(active + offset)$$

where the offset takes into account the intercept value.

4) blood glucose value at the calibration point (BG/cp) was determined by direct blood testing.

Other possible variables include, but are not limited to, temperature, iontophoretic voltage (which is inversely proportional to skin resistance), and skin conductivity.

Large data sets were generated by collecting signals using a transdermal sampling system that was placed in operative contact with the skin. The sampling system transdermally extracted the analyte from the biological system using an appropriate sampling technique (in this case, iontophoresis). The transdermal sampling system was maintained in operative contact with the skin to provide a near continual or continuous stream of signals.

The basis of the Mixtures of Experts was to break up a non-linear prediction equation (Equation 5, below) into several Expert prediction equations, and then to have a routine to switch between the different linear equations. For predicting blood glucose levels, three separate linear equations (Equations 6, 7, and 8) were used to represent blood glucose, with the independent variables discussed above of time, active, signal, blood glucose at a calibration point (BG/cp), and a constant ($t_i$).

The switching between equations 6, 7, and 8 was determined by the parameters $w_1$, $w_2$, and $w_3$ in equation 5, which was further determined by the parameters $d_1$, $d_2$, and $d_3$ as given by equations 9–14, where the individual experts had a linear form:

$$BG = w_1 BG_1 + w_2 BG_2 + w_3 BG_3 \quad (5)$$

wherein (BG) was blood glucose, there are three experts (n=3); $BG_i$ was the analyte predicted by Expert i; and $w_i$ was a parameter, and the individual Experts $BG_i$ were further defined by the expression shown as Equations 6, 7, and 8

$$BG_1 = p_1(\text{time}) + q_1(\text{active}) + r_1(\text{signal}) + s_1(BG|cp) + t_1 \quad (6)$$

$$BG_2 = p_2(\text{time}) + q_2(\text{active}) + r_2(\text{signal}) + s_2(BG|cp) + t_2 \quad (7)$$

$$BG_3 = p_3(\text{time}) + q_3(\text{active}) + r_3(\text{signal}) + s_3(BG|cp) + t_3 \quad (8)$$

wherein, $BG_i$ was the analyte predicted by Expert i; parameters include, time (elapsed time), active (active signal), signal (calibrated signal), and BG/cp (blood glucose value at a calibration point); $p_i$, $q_i$, $r_i$, and $s_i$ were coefficients; and $t_i$ was a constant; and further where the weighting value, $w_i$, was defined by the formulas shown as a cations 9, 10, and 11

$$w_1 = \frac{e^{d_1}}{e^{d_1} + e^{d_2} + e^{d_3}} \quad (9)$$

$$w_2 = \frac{e^{d_2}}{e^{d_1} + e^{d_2} + e^{d_3}} \quad (10)$$

$$w_3 = \frac{e^{d_3}}{e^{d_1} + e^{d_2} + e^{d_3}} \quad (11)$$

where e referred to the exponential function and $d_i$ was a parameter set (analogous to Equations 6, 7, and 8) that were used to determine the weights $w_i$, given by Equations 9, 10, and 11, and $$d_1 = \tau_1(\text{time}) + \beta_1(\text{active}) + \gamma_1(\text{signal}) + \delta_1(BG|cp) + \epsilon_1 \quad (12)$$

$$d_2 = \tau_2(\text{time}) + \beta_2(\text{active}) + \gamma_2(\text{signal}) + \delta_2(BG|cp) + \epsilon_2 \quad (13)$$

$$d_3 = \tau_3(\text{time}) + \beta_3(\text{active}) + \gamma_3(\text{signal}) + \delta_3(BG|cp) + \epsilon_3 \quad (14)$$

where $\tau_i$, $\beta_i$, $\gamma_i$ and $\delta_i$ were coefficients, and where $\epsilon_i$ is a constant.

To calculate the above parameters an optimization method was applied to the algorithm (Equations 5–14) and the large data set. The optimization method used was the Expectation Maximization method (Dempster, A. P., N. M. Laird, and D. B. Rubin, *J. Royal Statistical Society* (Series B-Methodological) 39:(1), 1977), but other methods may be used as well.

The parameters in these equations were determined such that the posterior probability of the actual glucose was maximized.

Example 2

Prediction of Measurement Values I

Iontophoretic extraction of glucose was carried out using a GlucoWatch® monitor which employs (i) a low-level iontophoretic current to extract glucose through patient's skin, and (ii) an electrochemical biosensor to detect the extracted glucose. Iontophoresis was carried out for 3 minute intervals and electrochemical detection was carried out for 7 minute intervals to result in 10 minute measurement cycles—thus generating collections of data (data sets) as described in Example 1.

The data that were used for this analysis were obtained by diabetic subjects each wearing a GlucoWatch® monitor over a 14 hour period. The MOE inputs consisted of the following parameters (described in Example 1): time, active, signal, blood glucose at a calibration point (BG/cp). These training data were used to determine the unknown parameters in the MOE using the Expectation Maximization Method. The output of the MOE algorithm was the measured value of blood glucose. Using a three hour time point for calibrating the GlucoWatch® monitor, the mean percentage error (MPE) between the actual blood glucose and the calculated (MOE predicted) blood glucose was 13%.

In a diabetic study consisting of 61 patients, the diabetic subjects' blood glucose ranged from 23–389 mg/dl. A protocol was followed whereby a subject (who had fasted since the previous midnight) came to a test site where the GlucoWatch® monitor was applied to the subject, started, and calibrated. Over the next 14 hours, the subject had normal meals and a finger prick blood sample was taken every 20 minutes for glucose determination ("actual glucose"). Blood glucose levels were measured using the HemoCue® meter (HemoCue AB, Sweden), which has an accuracy of ±10%.

Figure 6:
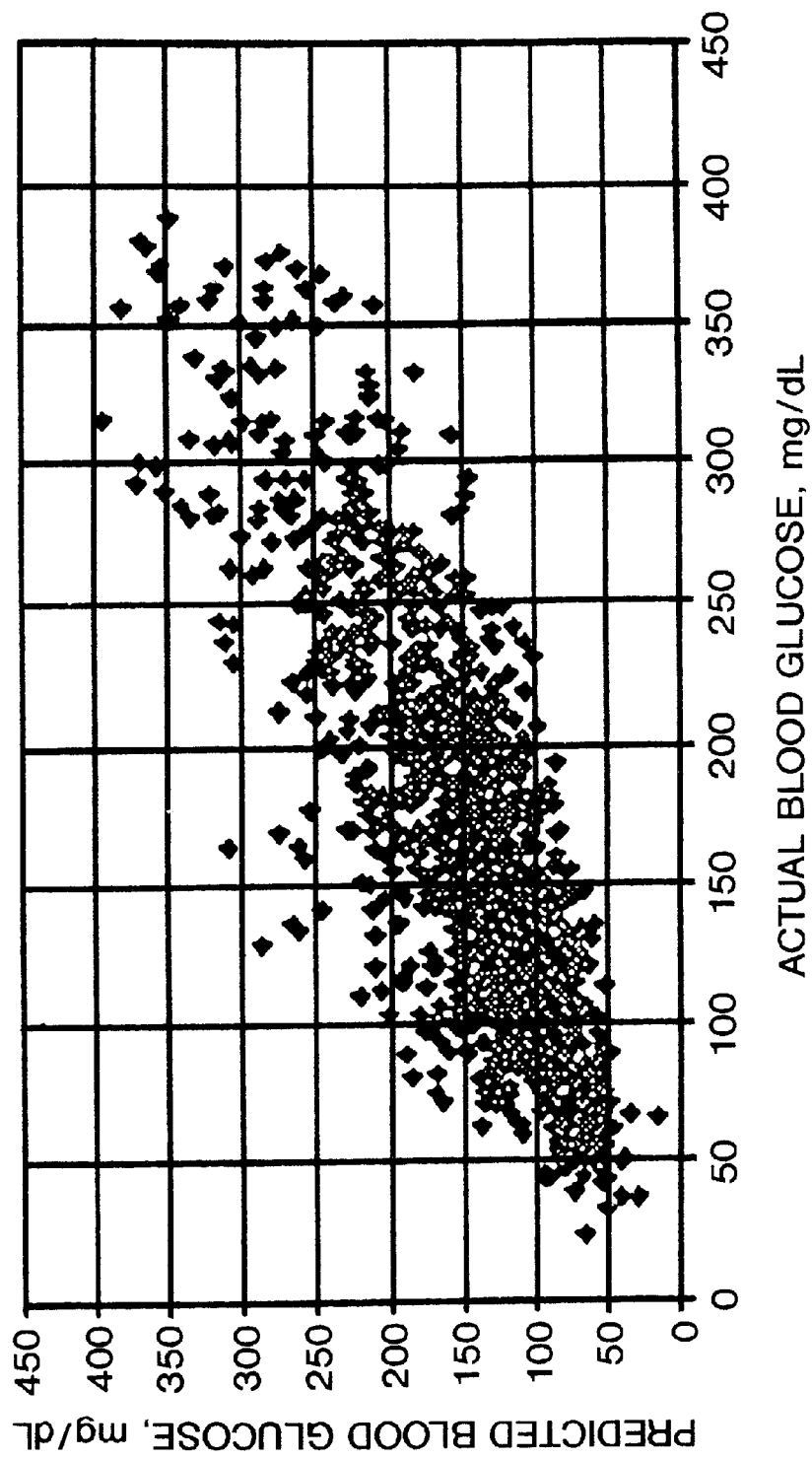
FIG. 6 depicts predicted blood glucose data (using the Mixtures of Experts algorithm) versus measured blood glucose data, as described in Example 2.

A plot of the glucose levels predicted by the Mixtures of Experts algorithm (based on the data described above) versus the actual blood glucose levels is presented in FIG. 6 (a Correlation Plot). Analysis of the data shown in FIG. 6 showed a slope of 0.88, an intercept of 14, and a correlation coefficient of R=0.93. There were N=1,348 points comprising the Correlation Plot.

These statistical results, along with the MPE=0.13 (discussed above), show the excellent predictive capabilities of the GlucoWatch® monitor and the Mixtures of Experts algorithm.

Example 3
Another Application of the "Mixtures of Experts" to Glucose Monitoring This example describes the use of a Mixtures of Experts (MOE) algorithm to predict blood glucose data from a series of signals.

In the present example, a GlucoWatch® monitor was used to collect data and the following variables were chosen to generate data sets for the MOE algorithm:

1) time since calibration (time$_c$), the elapsed time since the calibration step was carried out for the GlucoWatch® monitor (in hours);
2) active signal (active), in this example, the value of the active parameter corresponded to the averaged signal from two active reservoirs, where each reservoir provided a nanoamp signal that was integrated over the sensing time-interval, the two values were then added and averaged to give the active parameter in nanocoulombs (nC);
3) calibrated signal (signal), in this example was obtained as follows:

$$signal = \frac{BG/cp}{(active/cp + offset)}(active + offset)$$

where the offset takes into account the intercept value.
4) blood glucose value at the calibration point (BG/cp), in mg/dl, was determined by direct blood testing.

Other possible variables include, but are not limited to, temperature, iontophoretic voltage (which is inversely proportional to skin resistance), and skin conductivity.

Large data sets were generated by collecting signals using a transdermal sampling system that was placed in operative contact with the skin. The sampling system transdermally extracted the analyte from the biological system using an appropriate sampling technique (in this case, iontophoresis). The transdermal sampling system was maintained in operative contact with the skin to provide a near continual or continuous stream of signals.

The basis of the Mixtures of Experts was to break up a non-linear prediction equation (Equation 15, below) into several Expert prediction equations, and then to have a routine to switch between the different linear equations. For predicting blood glucose levels, three separate linear equations (Equations 16, 17, and 18) were used to represent blood glucose, with the independent variables discussed above of time, active, signal, blood glucose at a calibration point (BG/cp), and a constant ($t_i$).

The switching between Equations 16, 17, and 18 was determined by the parameters $w_i$, $w_2$, and $w_3$ in equation 5, which was further determined by the parameters $d_1$, $d_2$, and $d_3$ as given by equations 9–14, where the individual experts had a linear form:

$$BG = w_1 BG_1 + w_2 BG_2 + w_3 BG_3 \tag{15}$$

wherein (BG) was blood glucose, there are three experts (n=3); $BG_i$ was the analyte predicted by Expert i; and $w_i$ was a parameter, and the individual Experts $BG_i$ were further defined by the expression shown as Equations 16, 17, and 18

$$BG_1 = p_1(\text{time}_c) + q_1(\text{active}) + r_1(\text{signal}) + s_1(BG|cp) + t_1 \tag{16}$$

$$BG_2 = p_2(\text{time}_c) + q_2(\text{active}) + r_2(\text{signal}) + s_2(BG|cp) + t_2 \tag{17}$$

$$BG_3 = p_3(\text{time}_c) + q_3(\text{active}) + r_3(\text{signal}) + s_3(BG|cp) + t_3 \tag{18}$$

wherein, $BG_i$ was the analyte predicted by Expert i; parameters include, time$_c$ (elapsed time since calibration), active (active signal), signal (calibrated signal), and BG/cp (blood glucose value at a calibration point); $p_i$, $q_i$, $r_i$, and $s_i$ were coefficients; and $t_i$ was a constant; and further where the weighting value, $w_i$, was defined by the formulas shown as Equations 19, 20, and 21

$$w_1 = \frac{e^{d_1}}{e^{d_1} + e^{d_2} + e^{d_3}} \tag{19}$$

$$w_2 = \frac{e^{d_2}}{e^{d_1} + e^{d_2} + e^{d_3}} \tag{20}$$

$$w_3 = \frac{e^{d_3}}{e^{d_1} + e^{d_2} + e^{d_3}} \tag{21}$$

where e referred to the exponential function and $d_i$ was a parameter set (analogous to Equations 16, 17, and 18) that were used to determine the weights $w_i$, given by Equations 19, 20, and 21, and $$d_1 = \tau_1(\text{time}_c) + \beta_1(\text{active}) + \gamma_1(\text{signal}) + \delta_1(BG|cp) + \epsilon_1 \tag{22}$$

$$d_2 = \tau_2(\text{time}_c) + \beta_2(\text{active}) + \gamma_2(\text{signal}) + \delta_2(BG|cp) + \epsilon_2 \tag{23}$$

$$d_3 = \tau_3(\text{time}_c) + \beta_3(\text{active}) + \gamma_3(\text{signal}) + \delta_3(BG|cp) + \epsilon_3 \tag{24}$$

where $\tau_i$, $\beta_i$, $\gamma_i$ and $\delta_i$ were coefficients, and where $\epsilon_i$ is a constant.

To calculate the above parameters an optimization method was applied to the algorithm (Equations 15–24) and the large data set. The optimization method used was the Expectation Maximization method (Dempster, A. P., N. M. Laird, and D. B. Rubin, *J. Royal Statistical Society* (Series B-Methodological) 39:(1), 1977), but other methods may be used as well.

The parameters in these equations were determined such that the posterior probability of the actual glucose was maximized.

Example 4
Prediction of Measurement Values II
A. Calibration Ratio Check In order to insure an efficacious calibration of the sampling system, the value of the following ratio was found to fall in a selected range:

$$CalRatio = \frac{BG/cp}{(active/cp + offset)}$$

where the offset takes into account the intercept value. The range is established using standard error minimization routines to evaluate a large population of calibration points, and thereby determine the CalRatio values which result in accurate blood glucose predictions. In one embodiment, the preferred CalRatio range of values was between 0.00039 and 0.01. In the CalRatio, BG/cp was the blood glucose concentration at the calibration point (or calibration time), active was the input prediction at the calibration point, and offset was a constant offset. The offset value was established empirically using standard error minimization routines to evaluate a number of potential offset values for a large data set, and thereby select the one that results in the most accurate prediction of blood glucose.

The CalRatio check provides a screen for valid or efficacious calibration readings. If the CalRatio falls outside of the range of selected values, then the calibration was rejected and the calibration was re-done. Low values of this ratio indicated low sensitivity of glucose detection.

B. Prediction of Values

GlucoWatch® monitors (Cygnus, Inc., Redwood City, Calif., USA) were applied to the lower forearm of human subjects with diabetes (requiring insulin injection). Iontophoretic extraction of glucose was carried out using the GlucoWatch® monitor which employs (i) a low-level iontophoretic current to extract glucose through patient's skin, and (ii) an electrochemical biosensor to detect the extracted glucose.

The subjects were 18 years of age, or older, and consisted of both males and females from a broad ethnic cross-section. Iontophoresis was carried out for 3 minute intervals and electrochemical detection was carried out for 7 minute intervals to result in 10 minute measurement cycles—thus generating collections of data (data sets) as described in Example 3. As described in Example 3, the active measurement was the averaged signal from two active reservoirs, for example, a first electrode acts as the cathode during the first 10 minute cycle (3 minutes of iontophoresis, followed by 7 minutes of sensing) and a second electrode acts as the cathode during the second 10 minute cycle. The combined cycle requires 20 minutes, and the combined cathode sensor data is used as a measure of the glucose extracted (an averaged "active signal", see Example 3). This 20 minute cycle is repeated throughout operation of the GlucoWatch® monitor.

In addition, subjects obtained two capillary blood samples per hour, and the glucose concentration was determined using a HemoCue® clinical analyzer (HemoCue AB, Sweden). The blood glucose measurement obtained at three hours was used as a single point calibration, which was used to calculate the extracted blood glucose for all subsequent GlucoWatch® monitor measurements.

The data that were used for this analysis were obtained by diabetic subjects each wearing two GlucoWatch® monitors over a 14 hour period. The MOE inputs consisted of the following parameters (described in Example 3): $timer_c$, active, signal, blood glucose at a calibration point (BG/cp). For the calibrated signal:

$$signal = BG/cp \frac{(active + offset)}{(active/cp + offset)}$$

where (i) active/cp was the input prediction at the calibration point, and (ii) the offset and takes into account the fact that when predicted blood glucose is plotted vs. active, there is a non-zero y-intercept. The optimized value of the offset that was used was a constant value of 1000 nC. The signal that is used in the Mixtures of Experts algorithm is temperature compensated by applying an Arrhenius type correction to the raw signal data to account for skin temperature fluctuations.

Finally, in order to eliminate potential outlier points, various screens were applied to the raw and integrated sensor signals. The purpose of these screens were to determine whether certain environmental, physiological or technical conditions existed during a measurement cycle that could result in an erroneous reading. The screens that were used measured the averaged signal (active), iontophoretic voltage, temperature, and skin surface conductance. If any of these measurements deviated sufficiently from predefined behavior during a measurement, then the entire measurement was excluded. For example, if the skin surface conductance exceeded a set threshold, which indicated excessive sweating (sweat contains glucose), then this potentially erroneous measurement was excluded. These screens enable very noisy data to be removed, while enabling the vast majority of points (>87%) to be accepted.

The Mixtures of Experts was further customized in the following way. When the weights were updated using equations 19–24 (Example 3), a Laplacian distribution function was used. The Laplacian distribution has longer tails than a Gaussian distribution, and weighs deviations relative to the absolute difference from the mean, whereas a Gaussian distribution weighs deviations relative to the square of difference from the mean (P. McCullagh and J. A. Nelder, *Generalized Linear Models*, Chapman and Hall, 1989; and W. H. Press, S. A. Teukolsky, W. T. Vetterling and B. P. Flannery, *Numerical Recipes* in C. Cambridge University Press, Cambridge, 1992). In addition, the individual blood glucose values were weighted by the inverse of the value of the blood glucose at the calibration point. Both of these modifications result in increased accuracy of predictions, especially at low blood glucose levels.

The training data were used to determine the unknown parameters in the Mixtures of Experts using the Expectation Maximization Method. The Mixtures of Experts algorithm was trained until convergence of the weights was achieved. The output of the MOE algorithm was the measured value of blood glucose. Using a three hour time point for calibrating the GlucoWatch® monitor, the mean percentage error (MPE) between the actual blood glucose and the calculated (MOE predicted) blood glucose was 14.4%.

In a diabetic study consisting of 91 GlucoWatch® monitors, the diabetic subjects' blood glucose ranged from 40–360 mg/dl. A protocol was followed whereby a subject (who had fasted since the previous midnight) came to a test site where two GlucoWatch® monitors were applied to the subject, started, and calibrated. Over the next 14 hours, the subject had normal meals and a finger prick blood sample was taken every 20 minutes for glucose determination ("actual glucose"). Blood glucose levels were measured using the HemoCue® meter (HemoCue AB, Sweden), which has an accuracy of ±10%.

Figure 7:
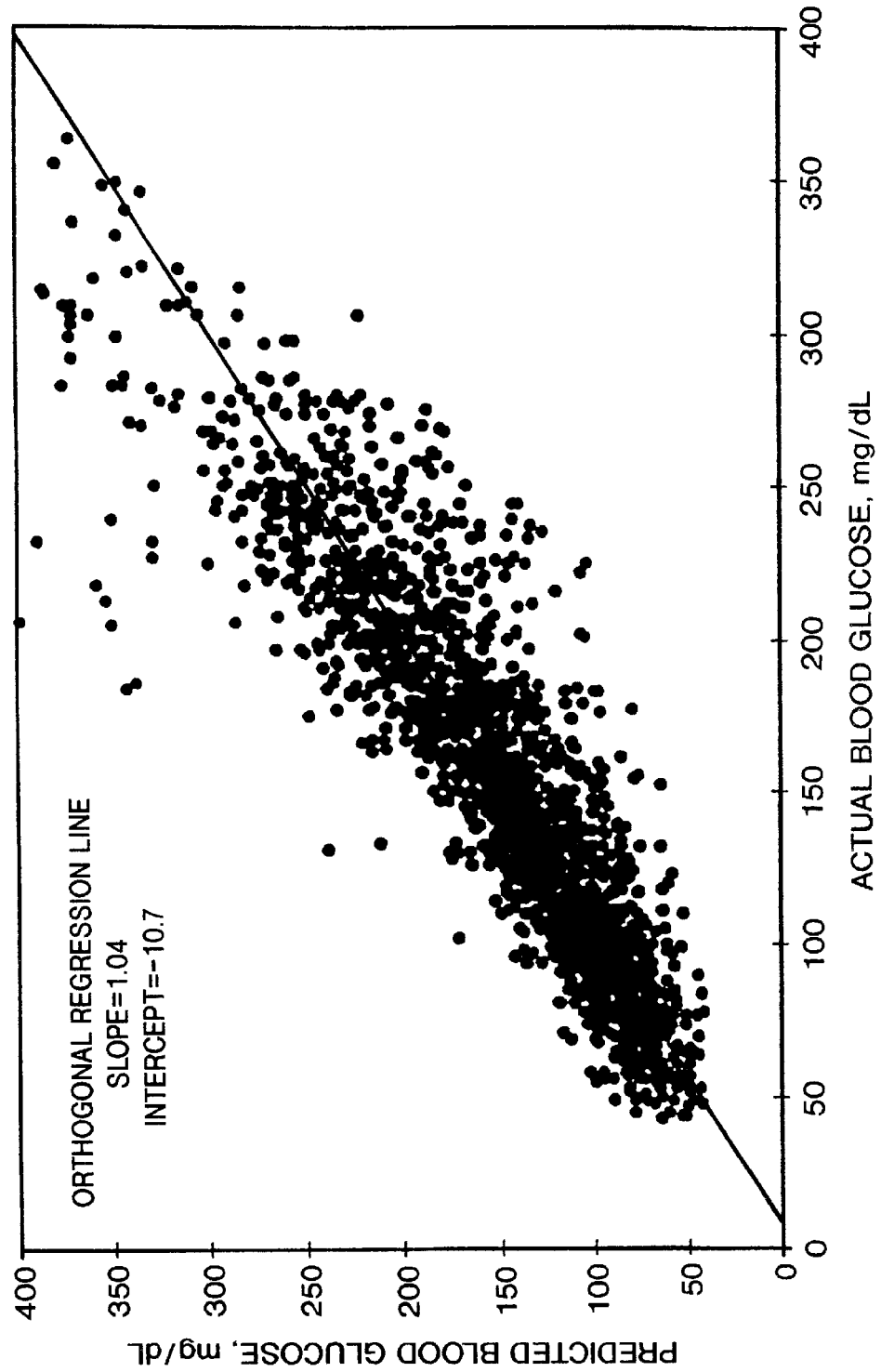
FIG. 7 depicts predicted blood glucose data (using the Mixtures of Experts algorithm) versus measured blood glucose data, as described in Example 4.

A plot of the glucose levels predicted by the Mixtures of Experts algorithm (based on the data described above) versus the actual blood glucose levels is presented in FIG. 7 (a Correlation Plot). Also shown in FIG. 7 is the orthogonal least squares line (A. Madansky, *The Fitting of Straight Lines When both Variables are Subject to Error*, J. American Statistical Association 54:173–206, 1959; D. York, *Least-Squares Fitting of a Straight Line*, Canadian Journal of Physics 44:1079–1986, 1966; W. A. Fuller, *Measurement Error Models*, Wiley, N.Y., 1987; and W. H. Press, S. A. Teukolsky, W. T. Vetterling and B. P. Flannery, *Numerical Recipes* in C. Cambridge University Press, Cambridge, 1992) with an error variance ratio (defined as the error in the dependent variable divided by the error of the independent variable) of 2.05. This variance error ratio corrects the linear regression line (which assumes zero error in the independent variable) for the true error in both independent and dependent variables.

The variance ratio was determined as follows. Each subject was required to wear two GlucoWatch® monitors. Then, at each time point, the difference between the two watches was determined, squared and divided by 2. The resulting values were averaged over the total number of time points used. Fifty pairs of watches, each with 42 time points, were used for this calculation. The error variance for the HemoCue® was obtained from clinical data published in the literature. The GlucoWatch® monitor error variance was calculated to be 150 (standard deviation=12 mg/dl) and the HemoCue® error variance was calculated to be 73 (standard deviation=8.5 mg/dl), giving the error ratio of 2.05.

Analysis of the data shown in FIG. 7 showed a slope of 1.04, an intercept of approximately −10.7 mg/dl, and a correlation coefficient of R=0.89.

Figure 8:
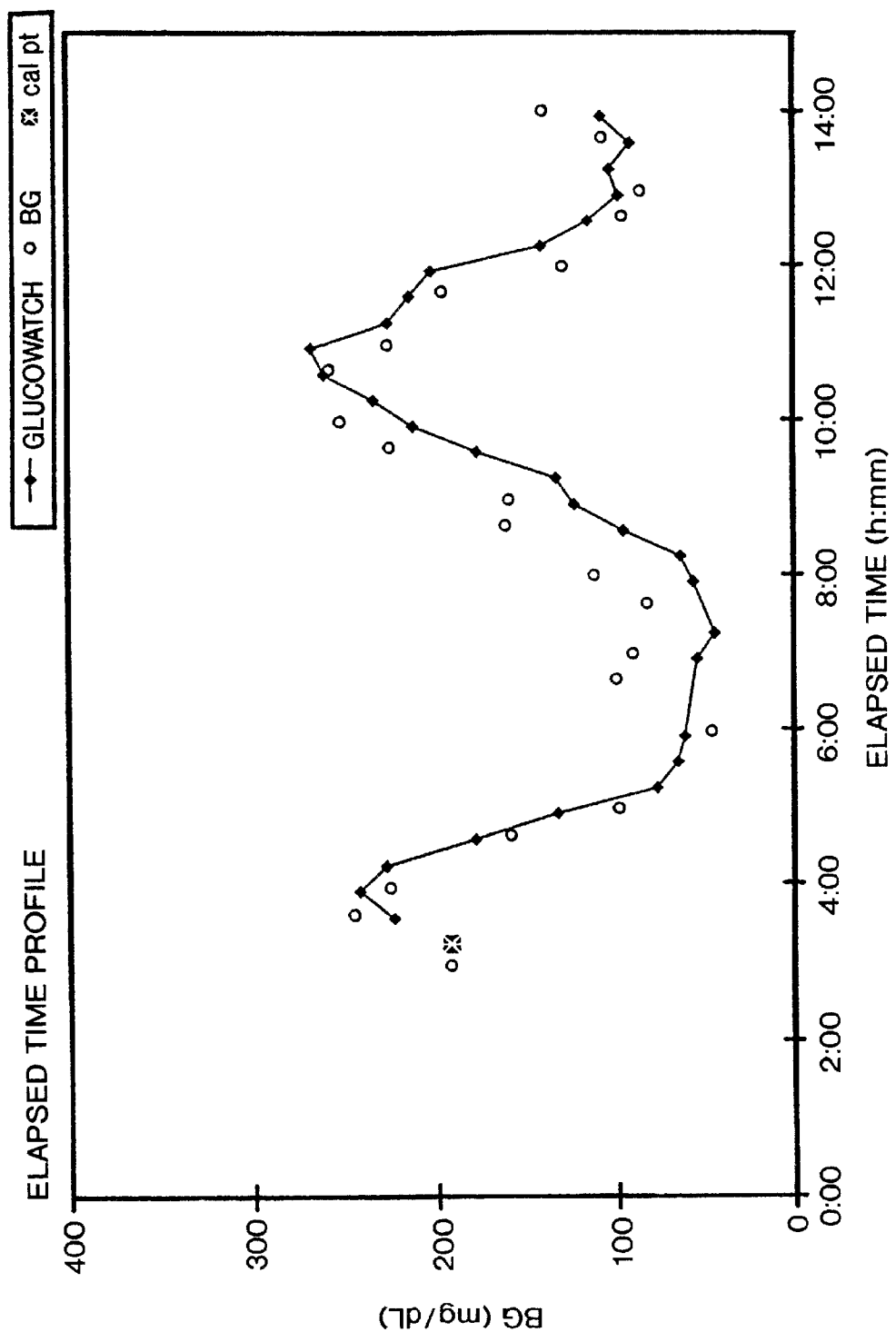
FIG. 8 presents a graph of the measured and predicted blood glucose levels vs. time, as described in Example 4.

It is also instructive to examine graphs of the measured and predicted blood glucose levels vs. time. One such graph is shown in FIG. 8 (in the legend of FIG. 8: solid diamonds are measurements obtained using the GlucoWatch® monitor; open circles are blood glucose concentrations as determined using HemoCue®; and the "star" symbol represents blood glucose concentration at the calibration point). FIG. 8 indicates the excellent capabilities of the GlucoWatch® monitor and the Mixtures of Experts algorithm in calibrating the device.

These statistical results, along with the MPE=14.4% (discussed above), show the excellent predictive capabilities of the GlucoWatch® monitor and the Mixtures of Experts algorithm.

Although preferred embodiments of the subject invention have been described in some detail, it is understood that obvious variations can be made without departing from the spirit and the scope of the invention as defined by the appended claims.

What is claimed is:

1. A method for measuring glucose present in a biological system, said method comprising:

transdermally extracting a sample comprising glucose from the biological system using a sampling system that is in operative contact with a skin or mucosal surface of said biological system;

obtaining a raw signal from the extracted glucose, wherein said raw signal is specifically related to glucose amount or concentration in the biological system;

performing a calibration which correlates the raw signal with a measurement value indicative of the amount or concentration of glucose present in the biological system at the time of extraction;

repeating said transdermal extracting and said obtaining a raw signal to obtain a series of two or more measurement values at selected time intervals; and predicting a measurement value based on the series of measurement values using a Mixtures of Experts algorithm comprising the following $$BG = w_1 BG_1 + w_2 BG_2 + w_3 BG_3 \quad (15)$$

wherein (BG) is blood glucose, $BG_i$ is the blood glucose predicted by Expert i; $w_i$ is a weighting value, and the individual Experts $BG_i$ are further defined by the expression shown as Equations 16, 17, and 18

$$BG_1 = p_1(\text{time}_c) + q_1(\text{active}) + r_1(\text{signal}) + s_1(BG|cp) + t_1 \quad (16)$$

$$BG_2 = p_2(\text{time}_c) + q_2(\text{active}) + r_2(\text{signal}) + s_2(BG|cp) + t_2 \quad (17)$$

$$BG_3 = p_3(\text{time}_c) + q_3(\text{active}) + r_3(\text{signal}) + s_3(BG|cp) + t_3 \quad (18)$$

wherein, $BG_i$ is the blood glucose predicted by Expert i; parameters include, $\text{time}_c$ (elapsed time from a calibration of said sampling system), active (active signal), signal (calibrated signal), and BG/cp (blood glucose value at a calibration point); $p_i$, $q_i$, $r_i$, and $s_i$ are coefficients; and $t_i$ is a constant; and further where the weighting value, $w_i$, is defined by the formulas shown as Equations 19, 20, and 21

$$w_1 = \frac{e^{d_1}}{e^{d_1} + e^{d_2} + e^{d_3}} \quad (19)$$

$$w_2 = \frac{e^{d_2}}{e^{d_1} + e^{d_2} + e^{d_3}} \quad (20)$$

$$w_3 = \frac{e^{d_3}}{e^{d_1} + e^{d_2} + e^{d_3}} \quad (21)$$

where e refers to the exponential function and $d_i$ is a parameter set used to determine the weights $w_i$, given by Equations 19, 20, and 21, and $$d_1 = \tau_1(\text{time}_c) + \beta_1(\text{active}) + \text{gamma}_1(\text{signal}) + \delta_1(BG|cp) + \epsilon_1 \quad (22)$$

$$d_2 = \tau_2(\text{time}_c) + \beta_2(\text{active}) + \text{gamma}_2(\text{signal}) + \delta_2(BG|cp) + \epsilon_2 \quad (23)$$

$$d_3 = \tau_3(\text{time}_c) + \beta_3(\text{active}) + \text{gamma}_3(\text{signal}) + \delta_3(BG|cp) + \epsilon_3 \quad (24)$$

where $\tau_i$, $\beta_i$, $\text{gamma}_i$ and $\delta_i$ are coefficients, and where $\epsilon_i$ is a constant.

2. The method of claim 1, wherein the sample is extracted from the biological system into a collection reservoir to obtain an amount or concentration of the glucose in said reservoir.

3. The method of claim 2, wherein the collection reservoir is in contact with the skin or mucosal surface of the biological system and the sample is extracted using an iontophoretic current applied to said skin or mucosal surface.

4. The method of claim 3, wherein the collection reservoir comprises an enzyme that reacts with the extracted glucose to produce an electrochemically detectable signal.

5. The method of claim 4, wherein the enzyme is glucose oxidase.

6. The method of claim 1, which includes further parameters for measurement values, said parameters selected from the group consisting of temperature, ionophoretic voltage, and skin conductivity.

7. A method for measuring glucose in a subject, said method comprising:

obtaining a raw signal from a sensing apparatus, wherein said raw signal is specifically related to an amount or concentration of glucose in the subject;

performing a calibration which correlates the raw signal with a measurement value indicative of the glucose amount or concentration in the subject;

repeating said obtaining of raw signal to obtain a series of measurement values at selected time intervals; and predicting a measurement value using a Mixtures of Experts algorithm comprising the following, $$BG = w_1 BG_1 + w_2 BG_2 + w_3 BG_3 \quad (15)$$

wherein (BG) is blood glucose, $BG_i$ is the blood glucose predicted by Expert i; $w_i$ is a weighting value, and the individual Experts $BG_i$ are further defined by the expression shown as Equations 16, 17, and 18

$$BG_1 = p_1(\text{time}_c) + q_1(\text{active}) + r_1(\text{signal}) + s_1(BG|cp) + t_1 \quad (16)$$

$$BG_2 = p_2(\text{time}_c) + q_2(\text{active}) + r_2(\text{signal}) + s_2(BG|cp) + t_2 \quad (17)$$

$$BG_3 = p_3(\text{time}_c) + q_3(\text{active}) + r_3(\text{signal}) + s_3(BG|cp) + t_3 \quad (18)$$

wherein, $BG_i$ is the blood glucose predicted by Expert i; parameters include, $\text{time}_c$ (elapsed time from a calibration of said sampling system), active (active signal), signal (calibrated signal), and BG/cp (blood glucose value at a calibration point); $p_i$, $q_i$, $r_i$, and $s_i$ are coefficients; and $t_i$ is a constant; and further where the weighting value, $w_i$, is defined by the formulas shown as Equations 19, 20, and 21

$$w_1 = \frac{e^{d_1}}{e^{d_1} + e^{d_2} + e^{d_3}} \quad (19)$$

$$w_2 = \frac{e^{d_2}}{e^{d_1} + e^{d_2} + e^{d_3}} \quad (20)$$

$$w_3 = \frac{e^{d_3}}{e^{d_1} + e^{d_2} + e^{d_3}} \quad (21)$$

where e refers to the exponential function and $d_i$ is a parameter set used to determine the weights $w_i$, given by Eguations 19, 20, and 21, and $$d_1 = \tau_1(\text{time}_c) + \beta_1(\text{active}) + \text{gamma}_1(\text{signal}) + \delta_1(BG|cp) + \epsilon_1 \quad (22)$$

$$d_2 = \tau_2(\text{time}_c) + \beta_2(\text{active}) + \text{gamma}_2(\text{signal}) + \delta_2(BG|cp) + \epsilon_2 \quad (23)$$

$$d_3 = \tau_3(\text{time}_c) + \beta_3(\text{active}) + \text{gamma}_3(\text{signal}) + \delta_3(BG|cp) + \epsilon_3 \quad (24)$$

where $\tau_i$, $\beta_i$, $\text{gamma}_i$ and $\delta_i$ are coefficients, and where $\epsilon_i$ is a constant.

8. The method of claim 7, wherein the sensing apparatus is a near-IR spectrometer.

9. The method of claim 7, wherein the sensing apparatus comprises a biosensor having an electrochemical sensing element.

10. The method of claim 7, wherein before said obtaining of a raw signal, a sample comprising glucose is extracted from the subject into a collection reservoir to obtain an amount or concentration of the glucose in said reservoir.

11. The method of claim 10, wherein the collection reservoir is in contact with the skin or mucosal surface of the biological system and the sample is transdermally extracted.

12. The method of claim 11, wherein said sample is extracted using an iontophoretic current applied to said skin or mucosal surface.

13. The method of claim 12, wherein the collection reservoir comprises an enzyme that reacts with the extracted glucose to produce an electrochemically detectable signal.

14. The method of claim 13, wherein the enzyme is glucose oxidase.

15. A monitoring system for measuring glucose present in a biological system, said monitoring system comprising, in operative combination:

a sampling device for extracting a sample comprising glucose from the biological system, wherein said sampling device extracts the sample across a skin or mucosal surface of said biological system;

a sensing device in operative contact with the sample extracted by the sampling device, wherein said sensing device obtains a raw signal from the extracted glucose and said raw signal is specifically related to an amount or concentration of glucose present in the biological system; and one or more microprocessors in operative communication with the sampling device and the sensing device, wherein said microprocessors (i) control the sampling device and the sensing device to obtain a series of raw signals at selected time intervals during a measurement period, (ii) correlate the raw signals with measurement values indicative of the amount or concentration of glucose present in the biological system, and (iii) predict a measurement value using a Mixtures of Experts algorithm comprising the following, $$BG = w_1 BG_1 + w_2 BG_2 + w_3 BG_3 \quad (15)$$

wherein (BG) is blood glucose, $BG_i$ is the blood glucose predicted by Expert i; $w_i$ is a weighting value, and the individual Experts $BG_i$ are further defined by the expression shown as Equations 16, 17, and 18

$$BG_1 = p_1(\text{time}_c) + q_1(\text{active}) + r_1(\text{signal}) + s_1(BG|cp) + t_1 \quad (16)$$

$$BG_2 = p_2(\text{time}_c) + q_2(\text{active}) + r_2(\text{signal}) + s_2(BG|cp) + t_2 \quad (17)$$

$$BG_3 = p_3(\text{time}_c) + q_3(\text{active}) + r_3(\text{signal}) + s_3(BG|cp) + t_3 \quad (18)$$

wherein, $BG_i$ is the blood glucose predicted by Expert i; parameters include, $\text{time}_c$ (elapsed time from a calibration of said sampling system), active (active signal), signal (calibrated signal), and BG/cp (blood glucose value at a calibration point); $p_i$, $q_i$, $r_i$, and $s_i$ are coefficients; and $t_i$ is a constant; and further where the weighting value, $w_i$, is defined by the formulas shown as Equations 19, 20, and 21

$$w_1 = \frac{e^{d_1}}{e^{d_1} + e^{d_2} + e^{d_3}} \quad (19)$$

$$w_2 = \frac{e^{d_2}}{e^{d_1} + e^{d_2} + e^{d_3}} \quad (20)$$

$$w_3 = \frac{e^{d_3}}{e^{d_1} + e^{d_2} + e^{d_3}} \quad (21)$$

where e refers to the exponential function and $d_i$ is a parameter set used to determine the weights $w_i$, given by Equations 19, 20, and 21, and $$d_1 = \tau_1(\text{time}_c) + \beta_1(\text{active}) + \text{gamma}_1(\text{signal}) + \delta_1(BG|cp) + \epsilon_1 \quad (22)$$

$$d_2 = \tau_2(\text{time}_c) + \beta_2(\text{active}) + \text{gamma}_2(\text{signal}) + \delta_2(BG|cp) + \epsilon_2 \quad (23)$$

$$d_3 = \tau_3(\text{time}_c) + \beta_3(\text{active}) + \text{gamma}_3(\text{signal}) + \delta_3(BG|cp) + \epsilon_3 \quad (24)$$

where $\tau_i$, $\beta_i$, $\text{gamma}_i$ and $\delta_i$ are coefficients, and where $\epsilon_i$ is a constant.

16. The monitoring system of claim 15, wherein the sampling device includes one or more collection reservoirs for containing the extracted sample.

17. The monitoring system of claim 16, wherein the sampling device uses an iontophoretic current to extract the sample from the biological system.

18. The monitoring system of claim 17, wherein the collection reservoir comprises an enzyme that reacts with the extracted glucose to produce an electrochemically detectable signal.

19. The monitoring system of claim 18, wherein the enzyme is glucose oxidase.

20. A monitoring system for measuring glucose in a subject, said system comprising, in operative combination:

a sensing device in operative contact with a sample extracted from the subject, said sample comprising glucose, wherein said sensing device obtains a raw signal specifically related to an amount or concentration of glucose in the subject; and one or more microprocessors in operative communication with the sensing device, wherein said microprocessors (i) control the sensing device to obtain a series of raw signals at selected time intervals, (ii) correlate the raw signals with measurement values indicative of the amount or concentration of glucose present in the subject, and (iii) predict a measurement value using a Mixtures of Experts algorithm comprising the following, $$BG = w_1 BG_1 + w_2 BG_2 + w_3 BG_3 \quad (15)$$

wherein (BG) is blood glucose, $BG_i$ is the blood glucose predicted by Expert i; $w_i$ is a weighting value, and the individual Experts $BG_i$ are further defined by the expression shown as Equations 16, 17, and 18

$$BG_1 = p_1(\text{time}_c) + q_1(\text{active}) + r_1(\text{signal}) + s_1(BG|cp) + t_1 \quad (16)$$

$$BG_2 = p_2(\text{time}_c) + q_2(\text{active}) + r_2(\text{signal}) + s_2(BG|cp) + t_2 \quad (17)$$

$$BG_3 = p_3(\text{time}_c) + q_3(\text{active}) + r_3(\text{signal}) + s_3(BG|cp) + t_3 \quad (18)$$

wherein, $BG_i$ is the blood glucose predicted by Expert i; parameters include, $\text{time}_c$ (elapsed time from a calibration of said sampling system), active (active signal), signal (calibrated signal), and BG/cp (blood glucose value at a calibration point); $p_i$, $q_i$, $r_i$, and $s_i$ are coefficients; and $t_i$ is a constant; and further where the weighting value, $w_i$, is defined by the formulas shown as Equations 19, 20, and 21

$$w_1 = \frac{e^{d_1}}{e^{d_1} + e^{d_2} + e^{d_3}} \quad (19)$$

$$w_2 = \frac{e^{d_2}}{e^{d_1} + e^{d_2} + e^{d_3}} \quad (20)$$

$$w_3 = \frac{e^{d_3}}{e^{d_1} + e^{d_2} + e^{d_3}} \quad (21)$$

where e refers to the exponential function and $d_i$ is a parameter set used to determine the weights $w_i$, given by Equations 19, 20, and 21, and $$d_1 = \tau_1(\text{time}_c) + \beta_1(\text{active}) + \text{gamma}_1(\text{signal}) + \delta_1(BG|cp) + \epsilon_1 \quad (22)$$

$$d_2 = \tau_2(\text{time}_c) + \beta_2(\text{active}) + \text{gamma}_2(\text{signal}) + \delta_2(BG|cp) + \epsilon_2 \quad (23)$$

$$d_3 = \tau_3(\text{time}_c) + \beta_3(\text{active}) + \text{gamma}_3(\text{signal}) + \delta_3(BG|cp) + \epsilon_3 \quad (24)$$

where $\tau_i$, $\beta_i$, $\text{gamma}_i$ and $\delta_i$ are coefficients, and where $\epsilon_i$ is a constant.

21. The monitoring system of claim 20, which includes further parameters for raw signals, said parameters selected from the group consisting of temperature, iontophoretic voltage, and skin conductivity.

22. The monitoring system of claim 20, wherein the sensing device comprises a biosensor having an electrochemical sensing element.

23. The monitoring system of claim 20, wherein the sensing device comprises a near-IR spectrometer.

* * * * *

UNITED STATES PATENT AND TRADEMARK OFFICE
CERTIFICATE OF CORRECTION

PATENT NO.   : 6,653,091 B1                                              Page 1 of 1
DATED        : November 25, 2003
INVENTOR(S)  : Timothy C. Dunn et al.

It is certified that error appears in the above-identified patent and that said Letters Patent is hereby corrected as shown below:

Column 41,
Line 41, "by Eguations 19," should read -- by Equations 19, --.

Signed and Sealed this

Twenty-fourth Day of February, 2004

JON W. DUDAS
*Acting Director of the United States Patent and Trademark Office*

Disclaimer 6,653,091 — Timothy C. Dunn, San Francisco, CA (US); Yalia Jayalakshmi, Sunnyvale, CA (US); Ronald T. Kurnik, Foster City, CA (US); Matthew J. Lesho, San Mateo, CA (US); Jonathan James Oliver, Oakland, CA (US); Russell O. Potts, San Francisco, CA (US); Janet A. Tamada, Mountain View, CA (US); Steven Richard Waterhouse, San Francisco, CA (US); Charles W. Wei, Fremont, CA (US). METHOD AND DEVICE FOR PREDICTING PHYSIOLOGICAL VALUES. Patent dated November 25, 2003. Disclaimer filed June 21, 2004, by the assignee, Cygnus, Inc.

The term of this patent, subsequent to the term of patent numbers, 6,326,160 and 6,180,416 has been disclaimed.

*(Official Gazette, November 2, 2004)*